United States Patent
Wu et al.

(10) Patent No.: US 11,369,654 B2
(45) Date of Patent: Jun. 28, 2022

(54) APPLICATION METHOD OF DENDROBIUM CANDIDUM IN PREPARING MEDICINE FOR TREATING HYPERTENSION

(71) Applicant: Hangzhou Danhe Pharmaceutical CO., Ltd., Zhejiang (CN)

(72) Inventors: Renzhao Wu, Hanzhou (CN); Yue Wu, Hanzhou (CN); Yu Chen, Hangzhou (CN)

(73) Assignee: Hangzhou Danhe Pharmaceutical Co., Ltd., Hangzhou (CN)

( * ) Notice: Subject to any disclaimer, the term of this patent is extended or adjusted under 35 U.S.C. 154(b) by 111 days.

(21) Appl. No.: 16/649,613

(22) PCT Filed: Aug. 23, 2018

(86) PCT No.: PCT/CN2018/102038
§ 371 (c)(1),
(2) Date: Mar. 20, 2020

(87) PCT Pub. No.: WO2019/056908
PCT Pub. Date: Mar. 28, 2019

(65) Prior Publication Data
US 2020/0268826 A1 Aug. 27, 2020

(30) Foreign Application Priority Data
Sep. 20, 2017 (CN) .......................... 201710855728.6

(51) Int. Cl.
*A61K 36/00* (2006.01)
*A61K 36/8984* (2006.01)
*A61P 9/12* (2006.01)
*A61K 9/00* (2006.01)

(52) U.S. Cl.
CPC ........ *A61K 36/8984* (2013.01); *A61K 9/0053* (2013.01); *A61P 9/12* (2018.01); *A61K 2236/333* (2013.01)

(58) Field of Classification Search
CPC ....................................................... A61P 9/12
See application file for complete search history.

(56) References Cited

FOREIGN PATENT DOCUMENTS

| CN | 101612316 A | * | 12/2009 |
| CN | 103690795 A | * | 4/2014 |
| CN | 103766905 A | * | 5/2014 |

* cited by examiner

*Primary Examiner* — Qiuwen MI
(74) *Attorney, Agent, or Firm* — Raymond Y. Chan; David and Raymond Patent Firm

(57) ABSTRACT

An application method of *Dendrobium candidum* in preparing a medicine for treating hypertension, includes: separately adding an adjuvant, according to a conventional medicine processing method, into *Dendrobium candidum* powder, or an extracting solution of *Dendrobium candidum* powder obtained by alcohol and water extraction, or a mixture of *Dendrobium candidum* powder and the extracting solution obtained by alcohol and water extraction, and preparing same as traditional Chinese medicine tablets, granules, suspended granules, pills, powder, or capsules, thereby obtaining a medicine for treating hypertension.

4 Claims, No Drawings

APPLICATION METHOD OF DENDROBIUM CANDIDUM IN PREPARING MEDICINE FOR TREATING HYPERTENSION

CROSS REFERENCE OF RELATED APPLICATION

This is a U.S. National Stage under 35 U.S.C. 371 of the International Application Number PCT/CN2018/102038, filed Aug. 23, 2018, which claims priority under 35 U.S.C. 119(a-d) to Chinese application number 201710855728.6, filed Sep. 20, 2017. The afore-mentioned patent applications are hereby incorporated by reference in their entireties.

BACKGROUND OF THE PRESENT INVENTION

Field of Invention

The present invention relates to the preparation technology of medicines or health food, and more particularly to the application of *Dendrobium officinale* in the preparation of health food or medicines for treating hypertension.

Description of Related Arts

Hypertension is a common high incidence in clinic, which has serious harm to heart, brain, kidney and other important organs. The 2013 China cardiovascular disease report estimates that there are about 270 million hypertension patients nationwide. The China Cardiovascular Disease Report of 2012 and 2013 shows that the mortality rate of cardiovascular diseases in China is 44.1%, ranking first in the death spectrum. Hypertension is the primary cause of cardiovascular and cerebrovascular diseases. Epidemiological survey results show that the mortality rate of cardiovascular and cerebrovascular diseases due to hypertension in China is increasing year by year. As far as stroke is concerned, there are more than 1.6 million new stroke patients and 6 million survivors in China every year, more than 75% of them lose their labor force, 45% of them are severely disabled and cannot take care of themselves.

Western medicine in the treatment of hypertension is still lack of drugs to adjust constitution and blood pressure (antihypertensive). The antihypertensive therapy in modern medicine is symptomatic. At present, the commonly used antihypertensive drugs include calcium channel blockers (CCB), angiotensin converting enzyme inhibitors (ACEI), angiotensin II receptor blockers (ARB), diuretics and beta blockers, which cannot completely prevent hypertension and its secondary development of the lesion. Most hypertensive patients need two or more antihypertensive prescriptions to achieve the target blood pressure, or it is difficult to reach the target blood pressure, most patients need to take medication for life. The efficacy of drugs gradually decreases due to the long course of medication, resulting in toxic and side effects, and these problems become more prominent with the extension of life. At present, the treatment of hypertension is still in urgent need of new and better medicines.

At present, the traditional Chinese medicine conditioning method for hypertension has certain advantages, but there are serious deficiencies. Although traditional Chinese medicine regulates hypertension, the speed and extent of blood pressure reduction is not as fast as western medicine, but it has the advantages of more stable and lasting curative effect, small blood pressure recovery after withdrawal, controlling blood pressure and improving overall physical fitness. Or conditioning to reduce blood pressure at the same time, but also can reduce blood lipids and so on, it has the advantages of adjusting physical fitness and improving various pathological indicators after improving physical fitness, has a certain application value. However, there are still some shortcomings, such as insufficient blood pressure in the near future after taking medicine, too many flavors of drugs which restrict or counteract each other, the prescription, extraction and preparation technology of drugs have not been systematically optimized and the curative effect cannot meet the requirements, so it is difficult to have practical application value in clinic.

When applying *Dendrobium officinale* to the treatment and health care of hypertension, there is a prejudice in technical understanding: it is believed that only a large amount of water can be extracted to improve the absorption and utilization of the active ingredients of the drug, and therefore the traditional method of *Dendrobium officinale* has the method of "Kuan Tang Jiu Jian" to improve the curative effect. There have been a patent using *Dendrobium officinale* aqueous extracts to prepare drugs for preventing or treating hypertension and stroke. However, the invention overcomes the traditional prejudice, in the treatment and health care application of hypertension, *Dendrobium officinale* adopts the alcohol and water extraction method, can greatly improve the short-acting antihypertensive effect; the long-acting hypotensive effect can be greatly improved by the powder application method than by the water extraction method, these two effects can be similar to that of amlodipine (adult 5 mg/day), the western medicine antihypertensive drug. The antihypertensive effect of its powder application method can surpass that of amlodipine at 24 hours after taking the medicine, and obtain unexpected curative effect.

SUMMARY OF THE PRESENT INVENTION

The invention is advantageous in that it provides an application method of *Dendrobium officinale* in preparing medicines for treating hypertension, so as to overcome the shortcomings and prejudices in the prior art.

Additional advantages and features of the invention will become apparent from the description which follows, and may be realized by means of the instrumentalities and combinations particularly pointing out in the appended claims.

According to the present invention, the foregoing and other objects and advantages are attained by a method for applying *Dendrobium officinale* in the preparation of a medicament for treating hypertension, comprising:

taking *Dendrobium officinale* according to the requirements of the 2015 edition of the Chinese Pharmacopoeia;

grinding to a powder form; and then according to the typical processing method of the pharmaceutical, adding the auxiliary material to prepare a traditional Chinese medicine tablet, granule or suspended granules, pills, powder or capsules, so as to obtain the drugs used to treat hypertension.

The invention also provides a method for using the medicine for treating hypertension prepared in the method that the prepared Chinese medicine tablets, granules or suspended granules, pills, powder or capsules are administered orally, and the daily dosage for adults is equivalent to the raw drug dosage of 4 g to 16 g.

The invention also provides an application method of the medicine for treating hypertension prepared in the method as a health food, that the prepared Chinese medicine tablets, granules or suspended granules, pills, powder or capsules are administered orally, and the daily dosage for adults is equivalent to the raw drug dosage of 4 g to 16 g.

In addition, the present invention also provides a method for applying the second *Dendrobium officinale* in the preparation of a medicament for treating hypertension, comprising the following steps.

(1) Take the *Dendrobium officinale* according to the requirements of the 2015 edition of the Chinese Pharmacopoeia, grind to powder and then carry out alcohol extraction: add 75% ethanol with 5 times the amount of crude drug is extracted at 60° C. for 24 hours, and extract twice to recover ethanol; after ethanol extraction, the residue is subjected by water extraction.

The water extraction is two gradient heating water extraction; wherein the extraction temperature is controlled to be 100° C. in the first water extraction, and the extraction temperature is controlled to be 121° C. in the second water extraction, and the two extraction solutions are combined.

The extracts are concentrated, and the alcohol extraction and water extraction are combined.

(2) The excipients are added to the combined extracts according to a typical pharmaceutical processing method, and prepared into Chinese medicine tablets, granules or suspended granules, pills, powders, oral liquids or capsules to obtain a medicament for treating hypertension.

The invention also provides a method for using the medicine for treating hypertension prepared in the method is characterized in that the prepared Chinese medicine tablets, granules or suspended granules, pills, powder, oral liquid or capsules are administered orally, and the daily dosage for adults is equivalent to the raw drug dosage of 4 g to 16 g.

The application method of the hypertensive medicine prepared in the method described as a health food, wherein the prepared Chinese medicine tablets, granules or suspended granules, pills, powder, oral liquid or capsules are administered orally, and the daily dosage for adults is equivalent to the raw drug dosage of 4 g to 16 g.

In addition, the invention also provides a third application method of *Dendrobium officinale* in the preparation of drugs for treating hypertension, including the following steps.

(1) According to the requirements of the 2015 edition of the Chinese Pharmacopoeia, ground *Dendrobium officinale* to a powder.

(2) Take half the weight of *Dendrobium officinale* powder for alcohol extraction: add 75% ethanol with 5 times the amount of crude drug, extract at 60° C. for 24 hours, and extract twice to recover ethanol; after ethanol extraction, the residue is subjected by water extraction.

The water extraction is two gradient heating water extraction; wherein the extraction temperature is controlled to be 100° C. in the first water extraction, and the extraction temperature is controlled to be 121° C. in the second water extraction, and the two extraction liquids are combined.

The extracts are concentrated, and the alcohol extraction and water extraction are combined.

(3) Add the remaining *Dendrobium officinale* powder to the combined extract in step (2), add the auxiliary material according to the conventional processing method of the pharmaceutical, and then prepare the traditional Chinese medicine tablets, granules or suspended granules, pills, powders, or capsules, and obtaining the treatment for the treatment hypertensive drugs.

The invention also provides a method for using the medicine for treating hypertension prepared in the method, wherein the prepared Chinese medicine tablets, granules or suspended granules, pills, powder, oral liquid or capsules are administered orally, and the daily dosage for adults is equivalent to the raw drug dosage of 4 g to 16 g.

The application method of the hypertensive medicine prepared in the method described as a health food, wherein the prepared Chinese medicine tablets, granules or suspended granules, pills, powder, oral liquid or capsules are administered orally, and the daily dosage for adults is equivalent to the raw drug dosage of 4 g to 16.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Hypertension in the theory of traditional Chinese medicine believes that most of them belong to yin deficiency and impotence, and yin and yang are the main treatment direction.

According to the theory and practice of Chinese medicine, refer to the 2015 edition of the Pharmacopoeia of the People's Republic of China: *Dendrobium officinale* has the properties of benefiting stomach and nourishing body fluid, nourishing yin and clearing heat. It can be used for fever, thirst, dry mouth, insufficient stomach Yin, less food and dry vomiting, deficiency and fever after illness, excessive Yin deficiency and fire, steaming and overheating of bones, obscure vision, impotence of muscles and bones. The existing technology is also used for the treatment of hypertension, but it has not been applied on a large scale because of its slow effect and insufficient hypotensive effect.

The traditional method of using *Dendrobium officinale* is limited by the traditional "widesoup for a long time", when using the *Dendrobium officinale* medicinal herbs after the "squatting", the method of directly adding water and boiling and extracting is carried out for clinical application. This usage, because the main ingredients of the herb are not easy to be decocted, its active ingredients (such as polysaccharides) are proposed in a very low proportion (about less than 10% of the weight of the herb can be obtained), and the efficacy of antihypertensive drugs is not ideal. In order to extract *Dendrobium officinale* by "crushing" with machine, the ratio of active ingredients (e.g. polysaccharides) is raised to a certain extent (about 20% polysaccharides of the weight of the medicinal materials could be obtained), and the effect of the method is also improved when it was used to reduce blood pressure. Most of the methods are used in industry. Traditional Chinese medicine in chemical production. (See Experiment 1).

In the research work of the present invention, the above extraction method has been greatly improved: the "powder" *Dendrobium officinale* medicinal materials are processed by machine, then extracted by adding water, and the extract is separated by solid-liquid separation technology. The proportion of active ingredients (e.g. polysaccharides) has raised significantly (about 40% of the weight of medicinal materials can be obtained). In the past, the extraction experiments of "tamping", "crushing" and "grinding powder" of *Dendrobium officinale* decoction pieces are carried out, and the same batch of medicinal materials are used for comparison. The effect of this method has been improved to some extent. This method is only preliminary used in the study of blood pressure reduction of *Dendrobium officinale*, and has not been applied in practice. However, it is found that although the antihypertensive effect of water extraction method after "grinding powder" is better than that after "crushing" and "tamping flat", there is still a long way to go to achieve the antihypertensive effect of amlodipine, at the same time, it is found that the effect of alcohol-water two-extraction method of *Dendrobium officinale* "grinding powder" followed by alcohol extraction and water extraction is greatly improved (within 1-3 hours after taking medicine), which reached and exceeded the effect of amlodipine, it is also found that the 24-hour antihypertensive effect and blood pressure stability of *Dendrobium officinale* powder taken directly are better.

The alcohol-water two-extraction method of *Dendrobium officinale* "grinding powder" followed by alcohol extraction and water extraction: the extraction and utilization of drug components is more complete than that of water alone, the absorption and utilization is faster, and the immediate (within 1-3 hours after taking medicine) antihypertensive effect is greatly improved.

Directly take *Dendrobium officinale* after "grinding powder": the drug ingredient utilization is more complete than water extraction and alcohol-water extraction. The drug gradually plays a role through digestion and absorption in vivo, which is equivalent to the "slow release" role of Chinese herbal medicine in the process of blood pressure reduction in vivo, and achieves a more stable 24-hour antihypertensive effect. (see Experiment 1 and 2).

The invention overcomes the traditional prejudice: the alcohol and water extraction method using alcohol extraction and water extraction can greatly improve the short-acting antihypertensive effect; the long-term antihypertensive effect can be greatly improved by the powder application method than by the water extraction method, the two effects are similar to that of amlodipine (5 mg/day for adults), the antihypertensive effect of the powder application method can exceed that of amlodipine 24 hours after taking medicine, and the unexpected curative effect has been achieved. The difference between the above three options is discussed in the following description The invention innovatively proposes three preparations for treating hypertension drugs, and the obtained drugs are all suitable for treating patients with hypertension of yin deficiency syndrome or yin deficiency and impotence syndrome; or the combination of western medicine antihypertensive drugs, reduce the use of western medicine antihypertensive drugs. At the same time, the three drugs are also suitable for the health care of patients with mild hypertension or normal hypertensive patients. More importantly, traditional Chinese medicine treatment of hypertension usually has a poor antihypertensive effect in terms of curative effect, and the antihypertensive effect rate is not fast enough, and the medicine of the present invention can obtain the similar effect to the western medicine antihypertensive drug, after taking the medicine, the partial antihypertensive effect also exceeds the western medicine antihypertensive drug. This is a very remarkable, unexpected technological effect that breaks through the imagination.

*Dendrobium officinale* powder: In addition to relatively saving medicinal materials, the antihypertensive effect is more stable and lasting than that of alcohol-water extraction in 24 hours, but the immediate antihypertensive effect is smaller than that of alcohol-water extraction. In general, *Dendrobium officinale* powder is used when the antihypertensive effect is stable and lasting.

*Dendrobium officinale* alcohol-water extraction: in addition to the smaller volume of the final drug, it can use a larger amount of crude drugs to improve the curative effect, and easy to take, the antihypertensive effect in 1.5-2.5 hours is greater than that of powder-in-drug method; but the antihypertensive effect in 24 hours is smaller than that of powder-in-drug method; in general, it needs to be faster than that of powder-in-drug method, the alcohol-water two-extraction method of *Dendrobium officinale* is used for depressurization.

*Dendrobium officinale* powder and *Dendrobium officinale* alcohol-water extraction: in the need for both rapid and stable sustained pressure reduction, the above two schemes are applied in a certain proportion.

It should be pointed out that, in view of the homology between traditional Chinese medicine and health products, and the fact that traditional Chinese medicine has no significant effect on normal blood pressure, it has good safety and can be used as health food. In most cases, there are only differences between traditional Chinese medicine and health food, and their substances are basically or even exactly the same. The products mentioned in the invention can be used as Chinese medicine for treating hypertension, as well as for daily health care of patients with mild hypertension or normal partial hypertension, and the use method is the same in both cases.

Compared with the prior art, the present invention has the following beneficial effects.

1. The invention adopts the traditional Chinese medicine *Dendrobium officinale* powder to make tablets, granules, pills, powders, or capsules, which is beneficial to exerting lasting and stable pharmacodynamics: (1) In the treatment of hypertension, drugs need to exert lasting and stable drug effect, Western antihypertensive drugs adopt sustained-release formulations, and the invention uses fine powder of medicinal materials to make tablets, granules (suspended granules), pills, powder or capsules to play the role of "pill slower" as mentioned in traditional Chinese medicine, so as to gradually dissolve medicines and play a lasting and stable sustained-release pharmacodynamics of traditional Chinese medicine; (2) *Dendrobium officinale* powder for raw use (different from the use of "long decoction"): also has a better "heat clearing" and "fire removing" effect, which is conducive to the reduction of blood pressure; (3) *Dendrobium officinale* is a precious medicinal material that needs to be fully utilized: the technical scheme of the invention fully considers the utilization of precious medicinal materials of *Dendrobium officinale*, reduces the waste caused by incomplete extraction, and also reduces the damage of some components caused by heating extraction process, so as to improve the curative effect and save precious medicinal materials.

2. In the alcohol and water extraction scheme of the invention, the comprehensive extraction method can reduce the loss of components and improve the effectiveness and the speed of exerting the curative effect than the conventional water extraction method: all medicinal materials are studied to increase the extraction contact surface; The alcohol-soluble substance is dissolved at a lower temperature condition, and the alcohol is extracted and then extracted with water. When the water is extracted, the alcohol-dissolving substance is no longer present, and the heating temperature at the time of water extraction does not affect the alcohol-dissolving substance, which is advantageous for improving the therapeutic effect.

3. Two-step gradient heating method was used for water extraction: water-soluble substances are routinely put forward when the first water extraction temperature was 100 C, and the adverse effects of excessive high temperature on the components were avoided; When the second water extraction temperature is 121° C., it is advantageous to propose substances that are resistant to high temperature but difficult to dissolve, such as long chain polysaccharides, degrading molecular weight, and advantageous to put forward, absorb and utilize.

4. It can selectively regulate hypertension without affecting normal blood pressure: it has the effect of lowering blood pressure on hypertension, but has no effect on normal blood pressure. Nor does it reduce hypertension below normal. This is also the advantage of the present invention over most western medicine antihypertensive drugs.

5. *Dendrobium officinale* regulates Yin deficiency and yang hyperactivity in order to treat hypertension as the "fundamental treatment": It cannot only reduce blood pressure quickly, but also stabilize blood pressure in the medium and long term, adjust and restore the balance of yin and yang. The Chinese herbal medicine can obtain similar curative effect with Western antihypertensive drugs, greatly expanding the application prospects of *Dendrobium officinale* in the treatment of hypertension.

SPECIFIC IMPLEMENTATION METHODS

Example 1

*Dendrobium officinale* Powder:

Take 500 g of *Dendrobium* in accordance with the 2015 edition of the Chinese Pharmacopoeia. The powder of *Dendrobium officinale* was ground and added with appropriate excipients according to the routine pharmacy to make Chinese medicine granules (suspended granules). Dry the medicine granules to obtain the sample for embodiment 1. The sample was administered by oral administration, the daily dosage of adults was equivalent to 8 g of crude drugs (can be as small as 4 g of crude drugs, can be as large as 16 g of crude drugs).

Example 2

Extraction of Alcohol and Water from *Dendrobium officinale*:

Take 500 g of *Dendrobium officinale* in accordance with Chinese Pharmacopoeia 2015 edition was extracted for 24 hours with 75% ethanol of 5 times the total amount of crude drugs at 60° C. for 2 times, and then the residue was extracted by water after ethanol extraction.

Water extraction was carried out by twice gradient heating method: the first water extraction: 30 times of the total amount of crude drug is added, and the extraction time was 2 hours at 100° C. Then carry out the second water extraction: 20 times of the total amount of crude drug added, and the second water extraction was carried out at 121° C. for 2 hours. And then, carry out the consolidation and concentration of Water Extracts.

After the alcohol extraction and the water extraction are separately concentrated, the extracts are combined, and appropriate excipients are added according to the pharmacy routine to prepare Chinese medicine granules. Dry the medicine granules to obtain the sample of example 2. The sample is administered by oral administration, the daily dose of adult is equivalent to 8 g of crude drug (can be as small as 4 g of crude drug, which can be as large as 16 g of crude drug).

Example 3

Extraction of *Dendrobium officinale* Powder with Alcohol and Water:

Take 250 g of *Dendrobium officinale* in accordance with the 2015 edition of the Chinese Pharmacopoeia, and research the fine powder of *Dendrobium officinale*.

Then take 250 g of *Dendrobium officinale* which conforms to the Chinese Pharmacopoeia of 2015 edition, grind fine powder of *Dendrobium officinale*, and then extract by alcohol. Extract twice by adding 75% ethanol of 5 times the amount of crude drug for 24 hours at 60° C., and then the residue is treated by water extraction after ethanol extraction. After carrying out the alcohol extraction and the water extraction, the extracted solutions in both of the processes of the alcohol extraction and water extraction are combined.

Two times of gradient heating extraction method are carried out in water extraction. Accordingly, in the first water extraction, add 30 times of the total amount of raw water, and extract 2 hours at 100° C. Time. In the second water extraction, add 20 times of the total amount of crude drug, and extract at 121° C. for 2 hours. And then carry out the consolidation and concentration of water Extracts.

The first extract of *Dendrobium officinale* 250 g fine powder and the second extract of *Dendrobium officinale* 250 g by ethanol and water are added with excipients according to the routine pharmaceutical processing method to make Chinese medicine granules (suspended granules) and dried to obtain samples for embodiment 3. The samples were administered by oral administration, the daily dosage of adults was equivalent to 8 g of crude drugs (can be as small as 4 g of crude drugs, can be as large as 16 g of crude drugs). The crude drug quantity in embodiment 3 is calculated by combining two crude drug quantities extracted by alcohol and water from *Dendrobium officinale* and *Dendrobium officinale* powder.

Experiment 1

Experimental Study on the Antihypertensive Effect of *Dendrobium officinale* Extraction on Spontaneously Hypertensive Rats (SHR)

[Experimental Materials]

Rats: Spontaneously Hypertensive Rats (SHR), Wistar rats are used as normal controls.

Test Chinese medicine: The following three extraction methods of *Dendrobium officinale* are used in the same batch of herbs.

Water extraction of *Dendrobium officinale* decoction pieces after flattening is described in the following description. Take 500 g of *Dendrobium officinale* in accordance with Chinese Pharmacopoeia 2015 edition is extracted. The water extraction is carried out after flattening the *Dendrobium officinale* with the common mallet. For the first time of water extraction, add water with 30 times of the total amount of crude drug and extract for 2 hours at 100° C. For the second time of water extraction, add 20 times of the total amount of crude drug water, extract at 100° C. for 2 hours. The water extract is concentrated and refrigerated for reserve. Compared with the traditional Chinese medicine decoction, the amount of water extracted by this method is greatly increased. The content of polysaccharide in the sample is 9.8% of the raw drug of *Dendrobium officinale* by phenol sulfate method as prescribed in Pharmacopoeia.

Water extraction from decoction pieces of *Dendrobium officinale* after crushing is discussed in the following description. Take 500 g of *Dendrobium officinale* in accordance with the 2015 edition of the Chinese Pharmacopoeia. Water extraction is carried out after crushing with the crushing machine. For the first time of water extraction, add water with 30 times of the total amount of crude drug and extract for 2 hours at 100° C. For the second time of water extraction, add 20 times of the total amount of crude drug water, extract at 100° C. for 2 hours. The water extract is concentrated and refrigerated for reserve. Compared with the traditional Chinese medicine decoction, the amount of water extracted by this method is greatly increased, and there is an additional "crushing" process before extraction. The content of polysaccharide in the sample is 20.3% of the raw drug of *Dendrobium officinale* by phenol sulfate method as prescribed in Pharmacopoeia.

Water Extraction from the decoction pieces of *Dendrobium officinale* after "grinding powder" is discussed in the following detailed description. Take 500 g of *Dendrobium officinale* in accordance with the 2015 edition of the Chinese Pharmacopoeia. The water extraction is carried out after machine grinding, for the first time of water extraction, add water of 30 times of the total amount of crude drug and extract for 2 hours at 100° C. For the second time of water extraction, add 20 times of the total amount of crude drug water, extract at 100° C. for 2 hours. The water extract is concentrated and refrigerated for reserve. Compared with the traditional Chinese medicine decoction, the amount of water extracted by this method is greatly increased, and there is an additional "grinding" process before extraction. The content of polysaccharide in the sample is 40.5% of the raw drug of *Dendrobium officinale* by phenol sulfate method as prescribed in Pharmacopoeia.

Western antihypertensive control drugs: amlodipine besylate tablets (Norvasc), 5 mg/tablets, batch number: R78401, produced by Pfizer Pharmaceutical Production.

Rat Blood Pressure Measurement: BP-98A Non-invasive Tail Artery Blood Pressure Meter, Japan Soft Rotation Co., Ltd.

[Experimental Method]

Group therapy is described in the following description. Blood pressure and body weight are measured and grouped after one week of adaptive feeding in all rats. The SHR rats are divided into the water extracting group after crushing and flattening, the water extracting group after crushing, and the water extracting group after grinding into powder, all Chinese medicine groups are given 0.8 g/kg body weight of crude drug, and the amlodipine besylate tablets 0.5 mg/kg body weight are given intragastrically in amlodipine group, the hypertensive model control group is given with the same amount of saline, while the normal control group is given with the same amount of saline. Eight rats in each group were treated for 2 weeks. Blood pressure measurement: The rats are preheated at 38° C. for 5-10 minutes to avoid blood flow in the tail of the rat. The blood pressure of the rats is measured three times in a waking and quiet state, and the average value of the three measurement times is used as the blood pressure of the rats. Blood pressure is measured once a week and once 2 hours after administration.

[Experimental Results]

The blood pressure data (x±S) are shown in Table 1 of Experiment 1 and Table 2 of Experiment 1.

At 2 weeks after treatment, blood pressure is measured 2 hours after administration, and the blood pressure of the powder water extraction group is 188.6±5.68/148.0±4.22 mmHg, which is significantly lower than that of the model group 209.3±6.89/160.3±5.67 mmHg (P<0.01/P<0.01), but Higher than the western medicine amlodipine group 175.5±4.48/143.7±4.28 mmHg, the difference in systolic blood pressure is significantly meaningful (P<0.05). The depressurization range of the flattening and water extraction group and the crushing and water extraction group is smaller than that of the grinding and water extraction group. The antihypertensive effect of *Dendrobium officinale* powder is relatively good, but the antihypertensive effect is lower than that of western medicine amlodipine. The water extract of *Dendrobium officinale* powder had better antihypertensive effect, but the antihypertensive effect is lower than that of amlodipine.

The dose of rats used in this experiment corresponds to the equivalent adult dose:

After flattening the decoction pieces of *Dendrobium officinale*, the corresponding adult dosage in the water extraction group is about 8 g everyday of raw drug of *Dendrobium officinale*;

After crushing the decoction pieces of *Dendrobium officinale*, the corresponding adult dosage in the water extraction group was about 8 g everyday of raw drug of *Dendrobium officinale*;

The corresponding adult dose in the water extract group after powder grinding of *Dendrobium officinale* decoction pieces is about 8 g everyday of raw drug of *Dendrobium officinale*;

The corresponding adult dose in amlodipine group is about 5 mg everyday for amlodipine besylate tablets.

[Conclusion]

The hypotensive effect of water extract group after powder grinding is greater than that of water extract group after crushing, and also greater than that of water extract group after flattening, but its hypotensive effect is lower than that of amlodipine.

Experiment 1: Table 1. Effect of different extraction methods of Dendrobium officinale on systolic blood pressure in SHR rats for 2 hours ($\bar{x} \pm S$; unit: mmHg; n = 8)

| Treatment time | Tamping water extraction | Crushing water extraction | Pulverized powder water extraction | Amlodipine | Model group | Normal group |
|---|---|---|---|---|---|---|
| Before treatment | 208.3 ± 8.23 | 207.6 ± 7.87 | 207.6 ± 8.24 | 206.3 ± 6.26 | 206.4 ± 7.40 | 142.6 ± 6.34▲ |
| Treatment for 1 week | 201.8 ± 6.78● | 197.4 ± 8.36● | 187.9 ± 6.87▲○ | 173.8 ± 5.26▲ | 208.4 ± 8.26● | 141.7 ± 5.26▲● |
| Treatment for 2 weeks | 202.5 ± 6.38● | 197.1 ± 5.36△● | 188.6 ± 5.68▲○ | 175.5 ± 4.48▲ | 209.3 ± 6.89● | 143.9 ± 6.24▲● |

Note:
Compared with the model group, △P < 0.05 ▲P < 0.01;
Amlodipine compared with each group ○P < 0.05 ●P < 0.01

Experiment 1: Table 2. Effect of different extraction methods of Dendrobium officinale on diastolic blood pressure in SHR rats for 2 hours ($\bar{x} \pm S$; unit: mmHg; n = 8)

| Treatment time | Tamping water extraction | Crushing water extraction | Pulverized powder water extraction | Amlodipine | Model group | Normal group |
|---|---|---|---|---|---|---|
| Before treatment | 159.8 ± 6.37 | 158.4 ± 6.26 | 157.8 ± 7.78 | 157.4 ± 5.67 | 156.2 ± 7.63 | 105.8 ± 6.87▲ |
| Treatment for 1 week | 155.4 ± 4.68● | 151.8 ± 5.27° | 147.4 ± 5.62▲ | 142.6 ± 5.78▲ | 159.6 ± 5.27● | 106.3 ± 7.37▲● |
| Treatment for 2 weeks | 156.5 ± 5.68● | 153.6 ± 4.79° | 148.0 ± 4.22▲ | 143.7 ± 4.28▲ | 160.3 ± 5.67● | 103.6 ± 5.78▲● |

Note:
Compared with the model group, $^\Delta P < 0.05$ $^\blacktriangle P < 0.01$;
Amlodipine compared with each group $^\circ P < 0.05$ $^\bullet P < 0.01$ Experiment 2

Experimental Study on Hypotensive Effect of Sample of Embodiment 1 and 2 on Spontaneously Hypertensive Rats (SHR)

[Experimental Materials]

Rats: 10 weeks old Spontaneously Hypertensive Rats (SHR), Wistar rats were used as normal controls.

Chinese medicine in the test is as follows.

Test sample of Example 1: Take 500 g of *Dendrobium* in accordance with the 2015 edition of the Chinese Pharmacopoeia, the powder of *Dendrobium officinale* is then ground and added with appropriate excipients according to the routine pharmacy to make Chinese medicine granules (suspended granules), dry the medicine granules to obtain the sample of example 1 and dissolve it in hot water before use.

Test sample of Example 2: 500 g of *Dendrobium officinale* in accordance with Chinese Pharmacopoeia 2015 edition is extracted for 24 hours with 75% ethanol of 5 times the total amount of crude drugs at 60° C. for 2 times, and then the residue is extracted by water after ethanol extraction, water extraction is carried out by twice gradient heating method, during the first time of water extraction, water with 30 times of the total amount of crude drug is added, and the extraction time is 2 hours at 100° C., then during the second time of water extraction: water with 20 times of the total amount of crude drug is added, and the second water extraction is carried out at 121° C. for 2 hours, and then, carry out the consolidation and concentration of water extracts, after the alcohol extraction and the water extraction, the extracts are combined, and appropriate excipients are added according to the pharmacy routine to prepare Chinese medicine granules, dry the medicine granules to obtain the sample of example 2 and dissolve it in hot water before use.

Alcohol extraction sample: Alcohol extraction is similar to the alcohol extraction in preparing the test sample of example 2. More specifically 500 g of *Dendrobium officinale* in accordance with Chinese Pharmacopoeia 2015 edition is extracted for 24 hours with 75% ethanol of 5 times the total amount of crude drugs at 60° C. for 2 times, the extracts are combined, concentrated and reserved.

Water extraction sample: Take 500 g of *Dendrobium officinale* in accordance with the 2015 edition of the Chinese Pharmacopoeia, and in the first time of water extraction, add water with 30 times of the total amount of raw drugs, extract 2 hours at 100° C., in the second time of water extraction, add water with 20 times the amount of raw drugs, extract at 100° C. for 2 hours, the water extracts are combined, concentrated and reserved.

Western antihypertensive control drugs: amlodipine besylate tablets (Norvasc), 5 mg/tablets, batch number: R78401, produced by Pfizer Pharmaceutical Production.

Rat Blood Pressure Measurement: BP-98A Non-invasive Tail Artery Blood Pressure Meter, Japan Soft Rotation Co., Ltd.

[Experimental Method]

Group therapy is described in the following description. Blood pressure and body weight are measured and grouped after one week of adaptive feeding in all rats. The SHR rats are divided into *Dendrobium officinale* alcohol extract sample group, *Dendrobium officinale* water extract sample group, the test sample group of embodiment 1, and the test sample group of embodiment 2, all Chinese medicine groups are given by 0.8 g/kg body weight of crude drug, and the amlodipine besylate tablets 0.5 mg/kg body weight are given intragastrically in amlodipine group, the hypertensive model control group is given with the same amount of saline, while the normal control group is given with the same amount of saline. Eight rats in each group are treated for 8 weeks. Blood pressure is observed for 1 week after withdrawal.

Blood pressure measurement: The rats are preheated at 38° C. for 5-10 minutes to avoid blood flow in the tail of the rat. The blood pressure of the rats is measured three times in a waking and quiet state, and the average value of three measurement times is used as the blood pressure of the rats. Blood pressure is measured twice a week, once 2 hours after administration and once 24 hours after administration, to observe the immediate antihypertensive effect and after 24 hours antihypertensive effect (and the peak-to-valley ratio).

The valley-peak ratio calculation of depressurization amplitude: The difference of blood pressure before treatment minus 24 hours after administration is the trough of the range of blood pressure reduction, which is the lowest point before the next administration; the difference of blood pressure before treatment and 2 hours after administration is the peak value of blood pressure reduction, that is, the maximum point of blood pressure reduction after administration. Valley value of depressurization amplitude divided by peak value of depressurization amplitude is equal to valley-peak ratio of depressurization amplitude. The closer the trough-peak ratio is to 1, the more stable the antihypertensive effect is, and the more in line with the requirements of long-term antihypertensive drugs; the closer the trough-peak ratio is to 0, the shorter the antihypertensive effect is.

[Experimental Results]

Blood pressure data (x±S) are shown in Table 1, Table 2, Table 3, Table 4 and Table 5 of Experiment 2.

1. Blood pressure at 1 week of treatment.

(1) Blood pressure 2 hours after administration.

The value of Example 2 group (alcohol and water extraction group) is 172.9±9.38/141.1±10.53 mmHg, which is very significantly lower than the model group 207.0±7.45/157.0±7.03 mmHg (P<0.01/P<0.01), and lower than the alcohol extraction group 181.4±5.22/146.8±9.60 mmHg (P<0.01/P>0.05), also lower than the water extraction group 180.0±7.26/143.7±7.56 mmHg (P<0.01/P>0.05). It is also slightly lower than the western medicine antihypertensive drug amlodipine group 175.1±4.44/143.2±6.41 mmHg, but there is no significant difference (P>0.05/P>0.05). The two-hour hypotensive effect of group 2 (ethanol-water two-extraction group) has exceeded that of water-extraction group and ethanol-extraction group in one week, and reached the hypotensive effect range of amlodipine group.

The value of Example 1 group (powder group) is 181.2±6.71/148.1±10.55 mmHg, which is significantly lower than the model group (P<0.01/P<0.05), but less than group 2 (alcohol-water two-extraction group).

(2) Blood pressure 24 hours after administration.

The value of Example 1 Group (powder group) is 189.7±10.26/149.3±9.05 mmHg, which is significantly lower than the model group 208.1±9.31/163.8±5.83 mmHg (P<0.05/P<0.01), and the pressure drop of the group of the example 2 group (alcohol and water extraction group), the water extraction group, the alcohol extraction group and the western medicine antihypertensive drug amlodipine group are larger.

The value of Example 2 Group (alcohol and water extraction group) is 203.2±12.69/161.5±13.54 mmHg, which is lower than the model group 208.1±9.31/163.8±5.83 mmHg, but has no significant difference (P>0.05/P>0.05).

(3) At 8 weeks of 24 hours of antihypertensive dose/2 hours of antihypertensive effect: trough-peak ratio of depressurization.

The value of trough-peak ratio of depressurization of the Example 1 group (powder group) is 0.71 which is 20.8 mmHg for 24 hours divided by 29.3 mmHg for 2 hour.

The value of trough-peak ration of depressurization of the water extract group is 0.25 which is the 24-hour hypotensive amplitude of 6.9 mmHg divided by the 2-hour hypotensive amplitude of 27.4 mmHg.

The value of trough-peak ration of depressurization of the ethanol extract group is 0.39 which is the 24-hour hypotensive amplitude of 10.1 mmHg divided by the 2-hour hypotensive amplitude of 26.0 mmHg was equal to the trough-peak ratio of 0.39.

The value of trough-peak ration of depressurization of the amlodipine group is 0.26 which is the 24-hour hypotensive amplitude was 9.1 mmHg divided by the 2-hour hypotensive amplitude of 34.7 mmHg.

The value of trough-peak ration of depressurization of the second group (ethanol-water extraction group) is 0.11 which is the 24-hour hypotensive amplitude of 3.8 mmHg divided by the 2-hour hypotensive amplitude of 34.1 mmHg.

At the first week of treatment, the 24-hour blood pressure reduction range of group 1 (powder group) is 20.8 mmHg higher than those of water extraction group (6.9 mmHg), alcohol extraction group (10.1 mmHg), alcohol-water extraction group (3.8 mmHg), and amlodipine group (9.1 mmHg). The trough-peak ratio of the first group (powder group) is 0.71 (71%) higher than those of the water extraction group (0.25 (25%), the ethanol extraction group (0.39) (39%), the ethanol-water two-extraction group (0.11%) and the amlodipine group (0.26 (26%). The trough value of depressurization amplitude has reached more than 70% of the peak value of depressurization amplitude, which has exceeded those of amlodipine group (26%) and *Dendrobium officinale* water extraction group (25%). The stability of 24-hour hypotension amplitude of example 1 (powder group) is significantly better than that of water extraction group and amlodipine group. In the example 2 group (ethanol-water two-extraction group), the 2-hour hypotension range of 34.1 mmHg is significantly better than that of 27.4 mmHg in the water-extraction group, and has reached the action range of 34.7 mmHg in the amlodipine group. The short-term hypotension effect is better than that of other groups.

2. Blood pressure at 8 weeks of treatment.

(1) Blood pressure 2 hours after administration.

The value of the group of Example 2 (alcohol and water extraction group) is 172.2±2.22/134.7±3.41 mmHg, which is significantly lower than the model group 212.3±5.37/159.7±5.48 mmHg (P<0.01/P<0.01), and is lower than the alcohol extraction group 178.0±4.14/141.7±1.92 mmHg (P<0.01/P<0.01), lower than the water extraction group 178.2±2.90/142.3±3.28 mmHg (P<0.01/P<0.01). It is also significantly lower than the western medicine antihypertensive drug amlodipine group 178.1±2.67/144.7±3.43 mmHg, (P<0.01/P<0.01). The 2-hour antihypertensive effect of the example 2 (alcohol and water-extracting group) has significantly exceeded the water-extracting group and the alcohol-extracting group at 8 weeks, and has exceeded the antihypertensive effect of the western medicine antihypertensive drug amlodipine group. The short-acting antihypertensive effect is superior to other groups.

The value of the Example 1 group (powder group) is 180.6±2.91/145.0±4.06 mmHg, which is significantly lower than the model group (P<0.01/P<0.01), However, compared with the example 2 group (alcohol and water extraction group), the pressure drop is smaller.

(2) Blood pressure 24 hours after administration.

The value of the Example 1 group (powder group) is 192.9±6.81/155.3±5.18 mmHg, which is significantly lower than the model group 217.0±6.39/165.4±4.16 mmHg (P<0.05/P<0.01), in comparison with the group of example 2 (alcohol and water extraction group) which is 201.3±3.01/156.5±4.21 mmHg, the water extraction group whose value is 203.4±2.76/160.2±6.14 mmHg, the alcohol extraction group whose value is 202.0±4.39/156.0±8.39 mmHg and the western medicine antihypertensive drug amlodipine group whose value is 202.0±5.88/154.3±5.50 mmHg, the depressurization amplitude of the Example 1 group is significantly larger (P<0.01/P>0.05).

The value of the depressurization amplitude of the group of example 2 (alcohol-water-extracting group) is significantly lower than that of the model group (p<0.01/p<0.01), but it is smaller than that of the example group 1 (powder group).

(3) At 8 weeks of treatment, the 24-hour hypotension amplitude divided by the 2-hour hypotension amplitude is equal to the trough-peak ratio of the hypotension amplitude.

In the example 1 group (powder group), the 24-hour antihypertensive amplitude of 17.6 mmHg divided by the 2-hour antihypertensive amplitude of 29.9 mmHg is equal to the trough-peak ratio of the antihypertensive amplitude which is 0.59.

In the water extract group, the 24-hour hypotensive amplitude of 4.0 mmHg divided by the 2-hour hypotensive amplitude of 29.2 mmHg is equal to the trough-peak ratio which is 0.14.

In the ethanol extract group, the 24-hour hypotension range of 5.4 mmHg divided by the 2-hour hypotension range of 29.4 mmHg is equal to the trough-peak ratio which is 0.18.

In the amlodipine group, the 24-hour hypotensive amplitude was 7.8 mmHg divided by 31.7 mmHg for 2 hours, which is equal to the trough-peak ratio which is 0.25.

In the example 2 group (ethanol-water two-extraction group), the 24-hour hypotensive amplitude of 5.7 mmHg divided by the 2-hour hypotensive amplitude of 34.8 mmHg is equal to the trough-peak ratio which is 0.16.

At the 8th week of treatment, the 24-hour blood pressure reduction range of group 1 (powder group) is 17.6 mmHg which is higher than those of group 4.0 mmHg in water extraction, 5.4 mmHg in alcohol extraction, 5.7 mmHg in alcohol-water extraction and 7.8 mmHg in amlodipine group. The trough-peak ratio of the first group (powder group) is 0.59 (59%) which is higher than those of the water extraction group (0.14 (14%), the alcohol extraction group (0.18 (18%), the alcohol-water two-extraction group (0.16% (16%) and the western medicine amlodipine group (0.25 (25%). The trough value of depressurization reached 50% of the peak value of depressurization, which is higher than that of amlodipine group (25%) and *Dendrobium officinale* water extraction group (14%). The stability of 24-hour hypotension amplitude of group 1 (powder group) is significantly better than that of water extraction group and amlodipine group. The two-hour hypotension range of group 2 (ethanol-water extraction group) was 34.8 mmHg, which is significantly better than that of water extraction group (29.2 mmHg), which was 31.7 mmHg of amlodipine group. The short-term hypotension effect is better.

3. Blood pressure 1 week after withdrawal.

(1) Blood pressure 3 days after stopping the drug.

The value of Example 2 group (alcohol and water extraction group) is 198.8±3.12/153.4±5.01 mmHg, very significantly lower than the model group whose value is 214.2±3.57/165.9±5.50 mmHg ($P<0.01/P<0.01$), and significantly lower than the water extraction group whose value is 205.2±2.83/156.1±2.71 mmHg ($P<0.05/P<0.05$), also significantly lower than the western medicine antihypertensive drug amlodipine group whose value is 205.4±1.85/158.7±2.79 mmHg, ($P<0.05/P>0.05$). The antihypertensive effect of the group 2 (alcoholic water-extracting group) after 3 days of drug withdrawal significantly has exceeded the antihypertensive effect of the water-extracting group and the western medicine antihypertensive drug amlodipine group. The value of the Example 1 group (powder group) is 199.6±3.24/152.1±5.77 mmHg, which is significantly lower than the model group whose value is 214.2±3.57/165.9±5.50 mmHg ($P<0.01/P<0.01$), which is similar to the pressure drop of the second group (alcohol and water).

Blood pressure 7 days after withdrawal:

The blood pressure of each group is significantly higher than that of the therapeutic drug, and the diastolic blood pressure is slower than the systolic blood pressure.

The diastolic blood pressure of group 2 (ethanol-water extraction group) is 153.0±3.24 mmHg), which is significantly lower than that of the water extraction group (165.5±3.13 mmHg, $P<0.01$) and the ethanol extraction group (161.6±5.53 mmHg, $P<0.05$).

The diastolic pressure of the group 1 (powder group) is 155.5±3.00 mmHg, which is significantly lower than that of the water extraction group (165.5±3.13 mmHg, $P<0.05$).

The western antihypertensive drug amlodipine group has a quick effect on lowering blood pressure, but the blood pressure rises quickly after withdrawal. From the blood pressure of 3 days after drug withdrawal, the blood pressure of group 1 (powder group) and group 2 (alcohol and water extraction group) increased slowly after drug withdrawal.

The dose of rats used in this experiment corresponds to the equivalent adult dose:

The corresponding adult dose of alcohol extraction sample group of *Dendrobium officinale* is about 8 g everyday of raw drug of *Dendrobium officinale*;

The corresponding adult dose of *Dendrobium officinale* water extract sample group is about 8 g everyday of raw drug of *Dendrobium officinale*;

The corresponding adult dose of group 1 (*Dendrobium officinale* powder group) is about 8 g everyday of raw drug of *Dendrobium officinale*;

The corresponding adult dose of group 2 (alcohol-water extract of *Dendrobium officinale*) is about 8 g/day of raw drug of *Dendrobium officinale candidum*.

The corresponding adult dose in amlodipine group was about 5 mg everyday for amlodipine besylate tablets.

[Conclusion]

The antihypertensive effect of sample 2 (extraction group of both ethanol and water) 2 hours after administration is significantly better than those of water extraction group of *Dendrobium officinale*, ethanol extraction group of *Dendrobium officinale* and ethanol extraction group of embodiment 1 (powder group), and also better than those of amlodipine group, a western medicine antihypertensive drug. The performance of depressurization has achieved or has exceeded the performance of the of western antihypertensive drug amlodipine. The performance of blood pressure rebound 3 days after withdrawal is slower than amlodipine. The sample of embodiment 2 is more suitable as a short-acting antihypertensive drug.

The antihypertensive effect of sample 1 (powder group) 24 hours after administration is significantly better than those of the water extract group, the alcohol extract group and the ethanol extract group of *Dendrobium officinale*, as well as that of group 2 (extraction group of both ethanol and water) of embodiment, and also better than those of the amlodipine group, and a western medicine antihypertensive drug. The ratio of trough to peak of hypotension is large, and the stability of hypotension reaches and surpasses amlodipine. The blood pressure rebound 3 days after withdrawal is slower than that of amlodipine. The sample of embodiment 1 is more suitable as a long-acting antihypertensive drug.

Experiment 2: Table 1. Effects of Samples from Executions 1 and 2 on Systolic Blood Pressure in SHR Rats after 2-hour Administration ($\bar{x} \pm S$; unit: mmHg; n = 8)

| Treatment time | alcohol extraction group | water extraction group | Example 1 group (Powder) | Example 2 group (alcohol and water) | Amlodipine | Model group | Normal group |
|---|---|---|---|---|---|---|---|
| Before treatment | 207.4 ± 6.66 | 207.4 ± 9.52 | 210.5 ± 6.80 | 207.0 ± 9.41 | 209.8 ± 8.92 | 208.4 ± 8.80 | 141.3 ± 3.44▲ |
| Treatment for 1 week | 181.4 ± 5.22▲★ | 180.0 ± 7.26▲★ | 181.2 ± 6.71▲★ | 172.9 ± 9.38▲● | 175.1 ± 4.44▲ | 207.0 ± 7.45●★ | 140.5 ± 4.05▲●★ |
| Treatment for 2 weeks | 181.8 ± 3.53▲☆ | 182.0 ± 2.02▲☆ | 181.0 ± 4.47▲ | 171.5 ± 5.17▲ | 178.3 ± 4.86▲ | 208.8 ± 7.83●★ | 139.1 ± 3.45▲●★ |
| Treatment for 3 weeks | 180.0 ± 3.28▲★ | 181.5 ± 2.19▲★ | 177.2 ± 6.38▲ | 172.7 ± 2.45▲ | 177.8 ± 5.31▲ | 205.7 ± 4.91●★ | 138.1 ± 4.57▲●★ |
| Treatment for 4 weeks | 181.6 ± 4.39▲★ | 184.0 ± 2.43▲★ | 180.8 ± 7.90▲ | 172.0 ± 3.42▲ | 175.7 ± 5.54▲ | 210.2 ± 7.15●★ | 139.2 ± 3.37▲●★ |
| Treatment for 5 weeks | 179.9 ± 2.81▲☆ | 180.0 ± 2.72▲☆ | 181.8 ± 1.80▲☆ | 176.2 ± 4.68▲○ | 174.3 ± 4.02▲ | 213.6 ± 3.03●★ | 138.3 ± 2.59▲●★ |
| Treatment for 6 weeks | 178.8 ± 2.42▲☆ | 179.2 ± 3.37▲☆ | 180.9 ± 1.89▲★ | 173.8 ± 3.25▲● | 178.8 ± 1.63▲ | 209.7 ± 3.89●★ | 139.6 ± 4.18▲●★ |
| Treatment for 7 weeks | 179.2 ± 2.08▲★ | 179.3 ± 2.57▲★ | 178.7 ± 1.46▲★ | 171.8 ± 2.69▲● | 175.8 ± 2.69▲ | 212.8 ± 5.34●★ | 141.3 ± 2.31▲●★ |
| Treatment for 8 weeks | 178.0 ± 4.14▲★ | 178.2 ± 2.90▲★ | 180.6 ± 2.91▲★ | 172.2 ± 2.22▲● | 178.1 ± 2.67▲★ | 212.3 ± 5.37●★ | 143.5 ± 3.39▲●★ |

Note: Compared with the model group, ▲P < 0.05 ▲P < 0.01;
Example 1 group (Powder) compared with each group ○P < 0.05 ●P < 0.01;
Example 2 group (alcohol and water) compared with each group ☆p < 0.05 ★p < 0.01

Experiment 2: Table 2. Effects of Samples from Executions 1 and 2 on Systolic Blood Pressure in SHR Rats after 24-hour Administration ($\bar{x} \pm S$; unit: mmHg; n = 8)

| Treatment time | alcohol extraction group | water extraction group | Example 1 group (Powder) | Example 2 group (alcohol and water) | Amlodipine | Model group | Normal group |
|---|---|---|---|---|---|---|---|
| Before treatment | 207.4 ± 6.66 | 207.4 ± 9.52 | 210.5 ± 6.80 | 207.0 ± 9.41 | 209.8 ± 8.92 | 208.4 ± 8.80 | 141.3 ± 3.44▲ |
| Treatment for 1 week | 197.3 ± 9.04 | 200.5 ± 11.31 | 189.7 ± 10.26▲ | 203.2 ± 12.69 | 200.7 ± 11.48 | 208.1 ± 9.31 | 139.7 ± 3.02▲●★ |
| Treatment for 2 weeks | 205.0 ± 9.28 | 208.6 ± 9.32● | 189.5 ± 7.44▲ | 203.8 ± 8.31 | 202.6 ± 11.80 | 211.0 ± 7.19● | 138.8 ± 3.94▲●★ |
| Treatment for 3 weeks | 203.4 ± 6.30▲● | 207.1 ± 5.61● | 191.5 ± 8.52▲★ | 205.2 ± 7.01▲● | 201.6 ± 7.07▲● | 212.6 ± 6.34●★ | 137.7 ± 5.14▲●★ |
| Treatment for 4 weeks | 207.1 ± 6.73● | 206.8 ± 9.47● | 191.3 ± 7.35▲★ | 205.1 ± 6.66● | 209.0 ± 7.09● | 211.0 ± 9.15● | 139.5 ± 3.38▲●★ |
| Treatment for 5 weeks | 210.0 ± 3.55● | 205.4 ± 7.09 | 194.3 ± 3.75▲☆ | 204.8 ± 5.53▲○ | 207.8 ± 7.95○ | 216.0 ± 4.83●☆ | 142.1 ± 3.61▲●★ |
| Treatment for 6 weeks | 204.8 ± 7.31 | 204.4 ± 9.81 | 190.9 ± 7.26▲ | 203.2 ± 7.44 | 202.8 ± 8.14 | 212.3 ± 4.52● | 142.1 ± 3.47▲●★ |
| Treatment for 7 weeks | 202.7 ± 6.59▲● | 202.4 ± 4.34▲● | 188.4 ± 2.89▲★ | 200.2 ± 6.86▲● | 199.5 ± 2.83▲● | 212.3 ± 6.02●★ | 142.5 ± 3.26▲●★ |
| Treatment for 8 weeks | 202.0 ± 4.39▲● | 203.4 ± 2.76▲● | 192.9 ± 6.81▲★ | 201.3 ± 3.01▲● | 202.0 ± 5.88▲● | 217.0 ± 6.39●★ | 141.8 ± 2.58▲●★ |
| Stopping for 3 days | 202.1 ± 1.40▲ | 205.2 ± 2.83▲☆ | 199.6 ± 3.24▲ | 198.8 ± 3.12▲ | 205.4 ± 1.85▲☆ | 214.2 ± 3.57●★ | 142.2 ± 2.48▲●★ |
| Stopping for 1 week | 214.8 ± 1.07 | 210.2 ± 7.42 | 212.8 ± 2.72 | 209.4 ± 2.98 | 214.2 ± 4.63 | 209.9 ± 4.06 | 142.8 ± 1.90▲●★ |

Note:
Compared with the model group, ▲P < 0.05 ▲P < 0.01;
Example 1 group (Powder) compared with each group ○P < 0.05 ●P < 0.01;
Example 2 group (alcohol and water) compared with each group ☆p < 0.05 ★p < 0.01

Experiment 2: Table 3. Effects of Samples from Executions 1 and 2 on diastolic Blood Pressure in SHR Rats after 2-hour Administration ($\bar{x} \pm S$; unit: mmHg; n = 8)

| Treatment time | alcohol extraction group | water extraction group | Example 1 group (Powder) | Example 2 group (alcohol and water) | Amlodipine | Model group | Normal group |
|---|---|---|---|---|---|---|---|
| Before treatment | 157.4 ± 6.36 | 155.6 ± 6.39 | 156.4 ± 6.86 | 156.9 ± 5.58 | 156.0 ± 4.47 | 157.1 ± 6.72 | 103.6 ± 7.50▲ |
| Treatment for 1 week | 146.8 ± 9.60Δ | 143.7 ± 7.56▲ | 148.1 ± 10.55Δ | 141.1 ± 10.53▲ | 143.2 ± 6.41▲ | 157.0 ± 7.03°★ | 107.9 ± 6.86▲●★ |
| Treatment for 2 weeks | 146.1 ± 5.79▲ | 145.0 ± 4.22▲ | 145.4 ± 7.78▲ | 141.0 ± 5.73▲ | 145.5 ± 10.08▲ | 160.6 ± 8.93●★ | 101.6 ± 6.76▲●★ |
| Treatment for 3 weeks | 147.6 ± 5.49▲☆ | 148.8 ± 3.05▲☆ | 146.2 ± 5.45▲ | 140.7 ± 6.89▲ | 144.7 ± 7.39▲ | 160.0 ± 8.02●★ | 96.7 ± 7.21▲●★ |
| Treatment for 4 weeks | 141.5 ± 13.07▲ | 149.3 ± 3.97▲☆ | 146.6 ± 8.46▲ | 140.1 ± 6.52▲ | 146.2 ± 8.50▲ | 163.9 ± 7.88●★ | 101.3 ± 2.82▲●★ |
| Treatment for 5 weeks | 145.4 ± 3.28▲★ | 147.0 ± 5.24▲★ | 147.2 ± 4.31▲★ | 138.6 ± 6.45▲● | 137.6 ± 6.45▲● | 162.5 ± 6.74●★ | 103.0 ± 2.28▲●★ |
| Treatment for 6 weeks | 142.2 ± 4.67▲☆ | 144.5 ± 5.15▲★ | 144.3 ± 4.66▲★ | 136.0 ± 6.61▲● | 143.1 ± 5.30▲☆ | 160.3 ± 6.85●★ | 102.3 ± 6.45▲●★ |
| Treatment for 7 weeks | 143.3 ± 3.20Δ☆ | 142.4 ± 2.77Δ☆ | 145.9 ± 4.02★ | 136.5 ± 2.54▲● | 139.9 ± 3.23▲ | 158.1 ± 8.45★ | 105.6 ± 5.83▲●★ |
| Treatment for 8 weeks | 141.7 ± 1.92▲★ | 142.3 ± 3.28▲★ | 145.0 ± 4.06▲★ | 134.7 ± 3.41▲● | 144.7 ± 3.43▲★ | 159.7 ± 5.48●★ | 100.8 ± 4.27▲●★ |

Note:
Compared with the model group, $^\Delta P < 0.05$ $^\blacktriangle P < 0.01$;
Example 1 group (Powder) compared with each group $^\circ P < 0.05$ $^\bullet P < 0.01$;
Example 2 group (alcohol and water) compared with each group $^\star p < 0.05$ $^\bigstar p < 0.01$ Experiment 2: Table 4. Effects of Samples from Executions 1 and 2 on diastolic Blood Pressure in SHR Rats after 24-hour Administration (x ± S; unit: mmHg; n = 8)

| Treatment time | alcohol extraction group | water extraction group | Example 1 group (Powder) | Example 2 group (alcohol and water) | Amlodipine | Model group | Normal group |
|---|---|---|---|---|---|---|---|
| Before treatment | 157.4 ± 6.36 | 155.6 ± 6.39 | 156.4 ± 6.86 | 156.9 ± 5.58 | 156.0 ± 4.47 | 157.1 ± 6.72 | 103.6 ± 7.50▲ |
| Treatment for 1 week | 155.1 ± 8.88 | 158.3 ± 9.53 | 149.3 ± 9.05▲☆ | 161.5 ± 13.54° | 162.3 ± 10.29° | 163.8 ± 5.83● | 105.3 ± 6.44▲●★ |
| Treatment for 2 weeks | 160.1 ± 8.13 | 157.6 ± 5.59 | 154.3 ± 11.32 | 159.6 ± 3.09 | 158.6 ± 8.39 | 162.2 ± 10.90 | 96.0 ± 10.36▲●★ |
| Treatment for 3 weeks | 161.7 ± 8.35 | 158.4 ± 10.06 | 157.4 ± 8.93 | 162.9 ± 6.82 | 159.0 ± 7.19 | 160.8 ± 7.32 | 99.8 ± 4.53▲●★ |
| Treatment for 4 weeks | 158.7 ± 6.11 | 162.6 ± 8.51● | 152.8 ± 5.83▲ | 157.0 ± 6.67Δ | 161.3 ± 7.00° | 164.1 ± 6.11●☆ | 102.3 ± 5.30▲●★ |
| Treatment for 5 weeks | 156.0 ± 8.73 | 154.8 ± 10.22Δ | 155.6 ± 5.99 | 158.8 ± 7.18 | 161.8 ± 5.19 | 162.8 ± 6.20 | 100.8 ± 8.07▲●★ |
| Treatment for 6 weeks | 157.3 ± 6.29 | 161.4 ± 6.02● | 152.7 ± 5.01▲★ | 162.0 ± 7.10● | 165.0 ± 6.96● | 162.2 ± 5.33● | 107.7 ± 7.04▲●★ |
| Treatment for 7 weeks | 159.3 ± 5.38 | 155.7 ± 8.50 | 151.1 ± 2.64A | 155.6 ± 5.94▲ | 156.3 ± 5.87Δ | 168.5 ± 3.43●★ | 108.1 ± 3.35▲●★ |
| Treatment for 8 weeks | 156.0 ± 8.39▲ | 160.2 ± 6.14 | 155.3 ± 5.18▲ | 156.5 ± 4.21▲ | 154.3 ± 5.50▲ | 165.4 ± 4.16●★ | 107.5 ± 4.87▲●★ |
| Stopping for 3 days | 149.6 ± 3.45▲ | 156.1 ± 2.71▲☆ | 152.1 ± 5.77▲ | 153.4 ± 5.01▲ | 158.7 ± 2.79Δ° | 165.9 ± 5.50●★ | 101.8 ± 7.03▲●★ |
| Stopping for 1 week | 161.6 ± 5.53☆ | 165.5 ± 3.13°★ | 155.5 ± 3.00 | 153.0 ± 3.24 | 155.4 ± 1.71 | 160.5 ± 6.67 | 105.5 ± 6.30▲●★ |

Note:
Compared with the model group, $^\Delta P < 0.05$ $^\blacktriangle P < 0.01$;
Example 1 group (Powder) compared with each group $^\circ P < 0.05$ $^\bullet P < 0.01$;
Example 2 group (alcohol and water) compared with each group $^\star p < 0.05$ $^\bigstar p < 0.01$ Experiment 2: Table 5. Effects of samples from executions 1 and 2 on valley-peak ratio of Systolic Blood Pressure Reduction in SHR rats 24 hours after Administration divided by 2 hours after Administration (x ± S; unit: mmHg; n = 8)

| Treatment time | alcohol extraction group | water extraction group | Example 1 group (Powder) | Example 2 group (alcohol and water) | Amlodipine |
|---|---|---|---|---|---|
| Before treatment | 207.4 ± 6.66 | 207.4 ± 9.52 | 210.5 ± 6.80 | 207.0 ± 9.41 | 209.8 ± 8.92 |
| Treatment for 1 week | 10.1/26.0 = 0.39 | 6.9/27.4 = 0.25 | 20.8/29.3 = 0.71 | 3.8/34.1 = 0.11 | 9.1/34.7 = 0.26 |
| Treatment for 2 weeks | 2.4/25.6 = 0.09 | −1.2/25.4 = 0 | 21.0/29.5 = 0.71 | 3.2/35.5 = 0.09 | 7.2/31.5 = 0.23 |
| Treatment for 3 weeks | 4.0/27.4 = 0.14 | 0.3/25.9 = 0.01 | 19.0/33.3 = 0.57 | 1.8/34.3 = 0.05 | 8.2/32.0 = 0.26 |
| Treatment for 4 weeks | 0.3/25.8 = 0.01 | 0.6/23.4 = 0.03 | 19.2/29.7 = 0.65 | 1.9/35.0 = 0.05 | 0.8/34.1 = 0.02 |
| Treatment for 5 weeks | −2.6/27.5 = 0 | 2.0/27.4 = 0.07 | 16.2/28.7 = 0.56 | 2.2/30.8 = 0.07 | 2.0/35.5 = 0.06 |
| Treatment for 6 weeks | 2.6/28.6 = 0.09 | 3.0/28.2 = 0.11 | 19.6/29.6 = 0.66 | 3.8/33.2 = 0.11 | 7.0/31.0 = 0.23 |
| Treatment for 7 weeks | 4.7/28.2 = 0.17 | 5.0/28.1 = 0.18 | 22.1/31.8 = 0.69 | 6.8/35.2 = 0.19 | 10.3/34.0 = 0.30 |
| Treatment for 8 weeks | 5.4/29.4 = 0.18 | 4.0/29.2 = 0.14 | 17.6/29.9 = 0.59 | 5.7/34.8 = 0.16 | 7.8/31.7 = 0.25 |

The trough-peak ratio of hypotension is the trough value of blood pressure reduction 24 hours after treatment divided by the peak value of blood pressure reduction 2 hours after treatment.

Experiment 3

Experimental Study on the Antihypertensive Effect of the Sample of Example 3 on Spontaneously Hypertensive Rats (SHR)

[Experimental Materials]

Rats: Spontaneously Hypertensive Rats (SHR), Wistar rats were used as normal controls.

Chinese medicine in the test is as follows.

The preparation of the test sample of Example 1 is discussed in the following details. Take 500 g of *Dendrobium* in accordance with the 2015 edition of the Chinese Pharmacopoeia. The powder of *Dendrobium officinale* is ground and added with appropriate excipients according to the routine pharmacy to make Chinese medicine granules (suspended granules). Dry the medicine granules to obtain the sample of example 1 and dissolve it in hot water before use.

The preparation of the test sample of Example 2 is discussed in the following details. 500 g of *Dendrobium officinale* in accordance with Chinese Pharmacopoeia 2015 edition is extracted for 24 hours with 75% ethanol of 5 times the total amount of crude drugs at 60° C. for 2 times, and then the residue is extracted by water after ethanol extraction. Water extraction is carried out by twice gradient heating method. During the first time of water extraction: add water with 30 times of the total amount of crude drug, and the extraction time is 2 hours at 100° C. Then during the second time of water extraction: add water with 20 times of the total amount of crude drug, and the second time of water extraction is carried out at 121° C. for 2 hours. And then carry out the consolidation and concentration of water extracts. After the alcohol extraction and the water extraction, the extracts are combined, and appropriate excipients are added according to the pharmacy routine to prepare Chinese medicine granules. Dry the medicine granules to obtain the sample of example 2 and dissolve it in hot water before use.

The preparation of the test sample of Example 3 is discussed in the following details. Take 250 g of *Dendrobium officinale* in accordance with the 2015 edition of the Chinese Pharmacopoeia, and research the fine powder of *Dendrobium officinale*. Then take 250 g of *Dendrobium officinale* which conforms to the Chinese Pharmacopoeia of 2015 edition, grind fine powder of *Dendrobium officinale*, and then extract by alcohol: Ethanol extraction is carried out twice by adding 75% ethanol of 5 times the amount of crude drug for 24 hours at 60° C., and then the residue is treated by water extraction after ethanol extraction. Alcohol extraction and water extraction are concentrated separately, then are combined. Two times of gradient heating extraction method for water extraction is carried out in the following manner. In the first time of water extraction: add water with 30 times of the total amount of raw drugs, and extract 2 hours at 100° C. Time. In the second time of water extraction, add water with 20 times of the total amount of crude drug, and extract at 121° C. for 2 hours. And then carry out the consolidation and concentration of water extracts. The first part of 250 g *Dendrobium officinale* which is in fine powder and the second part of 250 g *Dendrobium officinale* which is extracted by ethanol and water are added with excipients according to the routine pharmaceutical processing method to make Chinese medicine granules (suspended granules) and dried to obtain the sample of example 3, and dissolve it in hot water before use. (The crude drug amount of Example 3 is calculated by combining *Dendrobium officinale* powder and *Dendrobium officinale* alcohol-water.)

Western antihypertensive control drugs: amlodipine besylate tablets (Norvase), 5 mg/tablets, batch number R78401, produced by Pfizer Pharmaceutical Production.

Rat Blood Pressure Measurement: BP-98A Non-invasive Tail Artery Blood Pressure Meter, Japan Soft Rotation Co., Ltd.

[Experimental Method]

Group therapy is described in the following description. Blood pressure and body weight are measured and grouped after one week of adaptive feeding in all rats. The SHR rats were divided into the experimental sample group in embodiment 1, the experimental sample group in embodiment 2, the middle-dose group in embodiment 3, the low-dose group in embodiment 3, and the large-dose group in embodiment 3, each Chinese medicine group is given with 0.8, 0.8, 0.8, 0.4, and 1.6 g/kg body weight of crude drug respectively, the hypertensive model control group is given with the same amount of saline, while the normal control group is given with the same amount of saline. Eight rats in each group are treated for 2 weeks.

The following description discusses with the blood pressure measurement: The rats are preheated at 38° C. for 5-10 minutes to avoid blood flow in the tail of the rat. The blood pressure of the rats is measured three times in a waking and quiet state, and the average value of three times is used as the blood pressure of the rats. Blood pressure is measured twice a week, once 2 hours after administration and once 24 hours after administration, to observe the immediate anti-hypertensive effect and after 24 hours antihypertensive effect (and the trough-peak ratio).

The following description discusses with the trough-peak ratio calculation of depressurization amplitude. The difference of blood pressure before treatment minus 24 hours after administration is the trough of the range of blood pressure reduction, which is the lowest point before the next administration; the difference of blood pressure before treatment and 2 hours after administration is the peak value of blood pressure reduction, that is, the maximum point of blood pressure reduction after administration. Valley value of depressurization amplitude divided by peak value of depressurization amplitude is equal to valley-peak ratio of depressurization amplitude. The closer the trough-peak ratio is to 1, the more stable the antihypertensive effect is, and the more in line with the requirements of long-term antihypertensive drugs; the closer the trough-peak ratio is to 0, the shorter the antihypertensive effect is.

[Experimental Results]

Blood pressure data (x±S) is shown in Table 1, Table 2, Table 3, Table 4 and Table 5 of Experiment 3.

1. Blood pressure 2 hours after administration:

After 2 weeks of treatment at 2 weeks, the blood pressure of the embodiment 3 of middle dose (powder and alcohol) group is 182.3±3.13/143.1±3.35 mmHg, which is lower than that of the first group (powder group, 186.3±5.36/146.3±3.51 mmHg), higher than that of the second group (alcohol and water extract group, (172.2±4.87/140.6±4.69 mmHg), and higher than that of the second group (alcohol and water extract). The three groups are significantly lower than the model group (210.7±6.95/161.6±4.21 mmHg, P<0.05). The experimental results show that the blood pressure of the three groups of middle dose (grinding powder and alcohol-water) decreases 2 hours after administration. Compared with the group of 1 (grinding powder), the group of 1 (grinding powder) improves. The short-term hypotensive effect is accelerated by using part of grinding powder+part of ethanol and water as two extracts, which is faster than that of single medicinal powder.

For the Example 3, the blood pressure of the group of small doses (polishing powder+alcohol water) group is 189.7±5.10/149.1±4.35 mmHg, and the blood pressure of group 3 in the large dose (polishing powder+alcohol water) group is 169.5±4.16/139.6±4.71 mmHg, both of which are compared. There is a significant decrease in the model group (P<0.05 or P<0.01).

The blood pressure of the embodiment 3 of small dose (powder and alcohol) group is 189.7±5.10/149.1±4.35 mmHg, while the blood pressure of the three groups of large dose (powder and alcohol) group is 169.5±4.16/139.6±4.71 mmHg, which is significantly lower than that of the model group (P<0.05 or P<0.01).

2. Blood pressure 24 hours after administration.

24 hours after treatment at 2 weeks, the blood pressure of the embodiment 3 in the middle dose (powder and alcohol) group is 191.5±7.38/149.3±4.59 mmHg, which is slightly higher than that of the embodiment 1 in 189.7±6.44/147.3±3.78 mmHg, and lower than that of the embodiment 2 in 203.5±8.98/154.8±5.58 mmHg), which is significantly lower than that of the model group in 212.4±6.14/163.7±4.62 mmHg (P<0.05). The experimental results show that the blood pressure reduction of 24 hours after administration in the embodiments 3 is higher than that in the embodiments 2. The embodiments 2 are extracted with part of the medicinal powder and part of the medicinal material ethanol and water. On the basis of obtaining better short-term hypotensive effect, the embodiments 2 are extracted with more alcohol and water than those of the medicinal materials only. The drug also has increased the stability of 24-hour hypotensive effect.

The blood pressure of the embodiment 3 of small dose (powder and alcohol) group is 196.3±8.35/154.2±6.38 mmHg, while that of the embodiment 3 of large dose (powder and alcohol) group is 179.3±5.32/142.3±4.35 mmHg, which is significantly lower than that of the model group (P<0.05 or P<0.01). The large dose group has decreased blood pressure more significantly.

3. At 2 weeks of 24 hours of antihypertensive dose/2 hours of antihypertensive effect is trough-peak ratio of depressurization.

In the embodiments 1 group (powder group), the 24-hour antihypertensive amplitude of 20.2 mmHg divided by the 2-hour antihypertensive amplitude of 23.6 mmHg is equal to the trough-peak ratio of the antihypertensive amplitude which is 0.86.

In the embodiments 2 group (ethanol-water extraction group), the 24-hour antihypertensive amplitude of 5.4 mmHg divided by the 2-hour antihypertensive amplitude of 36.7 mmHg is equal to the trough-peak ratio of the antihypertensive amplitude which is 0.15.

In the medium dose of embodiments 3 group (grinding powder and alcohol-water extraction group), the 24-hour blood pressure reduction range of 16.8 mmHg in the middle dose group divided by the 2-hour blood pressure reduction range of 26.0 mmHg is equal to the trough-peak ratio which is 0.65.

In the low dose of embodiments 3 group (powder and alcohol-water extraction group), the 24-hour hypotensive amplitude of 13.2 mmHg divided by the 2-hour hypotensive amplitude of 19.8 mmHg is equal to the trough-peak ratio which is 0.67.

In the high dose of embodiments 3 group (powder and alcohol-water extraction group), the 24-hour hypotension amplitude of 28.3 mmHg divided by the 2-hour hypotension amplitude of 38.1 mmHg is equal to the trough-peak ratio which is 0.74;

After 2 weeks of treatment, the large, medium and small dose groups of embodiments 3 (grinding powder and alcohol-water extract group) obtained both 2-hour and 24-hour antihypertensive amplitude, and the trough-peak ratio of the antihypertensive amplitude over 0.65 (65%) is obtained.

The dose of rats used in this experiment corresponds to the equivalent adult dose.

The corresponding adult dose of the embodiments 1 group (powder group) is about 8 g everyday of raw drug of *Dendrobium officinale*.

The corresponding adult dose of the embodiments 2 group (ethanol-water extraction group) is about 8 g everyday of raw drug of *Dendrobium officinale*.

The corresponding adult dose of the medium dose of embodiments 3 group (grinding powder and alcohol-water extraction group) is about 8 g everyday of raw drug of *Dendrobium officinale*.

The corresponding adult dose of the low dose of embodiments 3 group (grinding powder and alcohol-water extraction group) is about 4 g everyday of raw drug of *Dendrobium officinale*.

The corresponding adult dose of the high dose of embodiments 3 group (grinding powder and alcohol-water extraction group) is about 16 g everyday of raw drug of *Dendrobium officinale*.

[Conclusion]

In the large, medium and small dose groups of the Example 3 sample (powder and alcohol-water extraction group), both the pressure reduction amplitude of the administration for 2 hours and the pressure reduction of the administration time of 24 hours are improved, and 0.65 (65%) is obtained, which is above the buck amplitude valley peak ratio.

Compared with the sample of embodiment 1 (powder group), the sample of embodiment 3 (powder and alcohol-water two-extraction group) has a larger 2-hour blood pressure reduction.

Compared with the sample of embodiment 2 (ethanol-water two-extraction group), the sample of embodiment 3 (powder and ethanol-water two-extraction group) has a larger 24-hour antihypertensive effect, and the antihypertensive effect is durable and stable.

Experiment 3: Table 1. Effects of Samples from Executions 3 on Systolic Blood Pressure in SHR Rats after 2-hour Administration ( x ± S; unit: mmHg; n = 8)

| Treatment time | Embodiments 3 groups low dose (grinding powder and alcohol-water) | Embodiments 3 groups medium dose (grinding powder and alcohol-water) | Embodiments 3 groups high dose (grinding powder and alcohol-water) | Embodiments 1 groups (grinding powder) | Embodiments 2 groups (alcohol-wate) | Model group | Normal group |
|---|---|---|---|---|---|---|---|
| Before treatment | 209.5 ± 5.68 | 208.3 ± 8.65 | 207.6 ± 7.81 | 209.9 ± 6.80 | 208.9 ± 8.36 | 207.8 ± 7.93 | 141.5 ± 5.33▲ |
| Treatment for 1 week | 190.2 ± 4.33▲★ | 179.1 ± 6.17▲ | 168.2 ± 3.84▲● | 185.6 ± 5.78▲★ | 173.8 ± 8.45▲● | 208.3 ± 6.34●★ | 140.5 ± 4.13▲●★ |
| Treatment for 2 weeks | 189.7 ± 5.10▲☆ | 182.3 ± 3.13▲☆ | 169.5 ± 4.16▲● | 186.3 ± 5.36▲★ | 172.2 ± 4.87▲● | 210.7 ± 6.95●★ | 139.7 ± 5.83▲●★ |

Note:

Compared with the model group, $^\Delta$P < 0.05 $^\blacktriangle$P < 0.01;

Example 1 group (Powder) compared with each group $^\circ$P < 0.05 $^\bullet$P < 0.01;

Example 2 group (alcohol and water) compared with each group $^\star$p < 0.05 $^\bigstar$p < 0.01

Experiment 3: Table 2. Effects of Samples from Executions 3 on Systolic Blood Pressure in SHR Rats after 24-hour Administration (x ± S; unit: mmHg; n = 8)

| Treatment time | Embodiments 3 groups low dose (grinding powder and alcohol-water) | Embodiments 3 groups medium dose (grinding powder and alcohol-water) | Embodiments 3 groups high dose (grinding powder and alcohol-water) | Embodiments 1 groups (grinding powder) | Embodiments 2 groups (alcohol-wate) | Model group | Normal group |
|---|---|---|---|---|---|---|---|
| Before treatment | 209.5 ± 5.68 | 208.3 ± 8.65 | 207.6 ± 7.81 | 209.9 ± 6.80 | 208.9 ± 8.36 | 207.8 ± 7.93 | 141.5 ± 5.33▲ |
| Treatment for 1 week | 195.5 ± 8.18 | 190.4 ± 8.27$^\Delta$ | 180.5 ± 6.36▲★ | 188.5 ± 8.14$^\Delta$ | 202.7 ± 9.46 | 209.5 ± 8.26° | 140.8 ± 4.34▲●★ |
| Treatment for 2 weeks | 196.3 ± 8.35 | 191.5 ± 7.38$^\Delta$ | 179.3 ± 5.32▲★ | 189.7 ± 6.44▲ | 203.5 ± 8.98 | 212.4 ± 6.14● | 139.6 ± 5.68▲●★ |

Note:

Compared with the model group, $^\Delta$P < 0.05 $^\blacktriangle$P < 0.01;

Example 1 group (Powder) compared with each group $^\circ$P < 0.05 $^\bullet$P < 0.01;

Example 2 group (alcohol and water) compared with each group $^\star$p < 0.05 $^\bigstar$p < 0.01

Experiment 3: Table 3. Effects of Samples from Executions 3 on Diastolic Blood Pressure in SHR Rats after 2-hour Administration (x ± S; unit: mmHg; n = 8)

| Treatment time | Embodiments 3 groups low dose (grinding powder and alcohol-water) | Embodiments 3 groups medium dose (grinding powder and alcohol-water) | Embodiments 3 groups high dose (grinding powder and alcohol-water) | Embodiments 1 groups (grinding powder) | Embodiments 2 groups (alcohol-wate) | Model group | Normal group |
|---|---|---|---|---|---|---|---|
| Before treatment | 159.2 ± 7.12 | 157.6 ± 5.37 | 158.1 ± 6.57 | 158.8 ± 6.78 | 159.5 ± 5.68 | 159.3 ± 7.36 | 104.7 ± 6.38▲ |
| Treatment for 1 week | 150.3 ± 3.38Δ | 144.7 ± 3.35▲ | 140.1 ± 4.51▲ | 148.1 ± 4.36Δ | 142.7 ± 5.37▲ | 160.3 ± 5.24○★ | 105.6 ± 7.68▲●★ |
| Treatment for 2 weeks | 149.1 ± 4.35Δ | 143.1 ± 3.35▲ | 139.6 ± 4.71▲ | 146.3 ± 3.51▲ | 140.6 ± 4.69▲ | 161.6 ± 4.21●★ | 103.3 ± 7.36▲●★ |

Note:
Compared with the model group, ΔP < 0.05 ▲P < 0.01;
Example 1 group (Powder) compared with each group ○P < 0.05 ●P < 0.01;
Example 2 group (alcohol and water) compared with each group ☆p < 0.05 ★p < 0.01

Experiment 3: Table 4. Effects of Samples from Executions 3 on Diastolic Blood Pressure in SHR Rats after 24-hour Administration (x ± S; unit: mmHg; n = 8)

| Treatment time | Embodiments 3 groups low dose (grinding powder and alcohol-water) | Embodiments 3 groups medium dose (grinding powder and alcohol-water) | Embodiments 3 groups high dose (grinding powder and alcohol-water) | Embodiments 1 groups (grinding powder) | Embodiments 2 groups (alcohol-wate) | Model group | Normal group |
|---|---|---|---|---|---|---|---|
| Before treatment | 159.2 ± 7.12 | 157.6 ± 5.37 | 158.1 ± 6.57 | 158.8 ± 6.78 | 159.5 ± 5.68 | 159.3 ± 7.36 | 104.7 ± 6.38▲ |
| Treatment for 1 week | 154.8 ± 7.37 | 150.1 ± 4.18Δ | 141.1 ± 5.03▲☆ | 148.2 ± 4.12▲ | 155.2 ± 4.17 | 161.3 ± 5.72● | 105.9 ± 7.36▲●★ |
| Treatment for 2 weeks | 154.2 ± 6.38 | 149.3 ± 4.59Δ | 142.3 ± 4.35▲☆ | 147.3 ± 3.78▲ | 154.8 ± 5.58 | 163.7 ± 4.62● | 103.2 ± 9.14▲●★ |

Note:
Compared with the model group, ΔP < 0.05 ▲P < 0.01;
Example 1 group (Powder) compared with each group ○P < 0.05 ●P < 0.01;
Example 2 group (alcohol and water) compared with each group ☆p < 0.05 ★p < 0.01

Experiment 3: Table 5. Effects of samples from executions 3 on valley-peak ratio of Systolic Blood Pressure Reduction in SHR rats 24 hours after Administration divided by 2 hours after Administration (x ± S; unit: mmHg; n = 8)

| Treatment time | Embodiments 3 groups low dose (grinding powder and alcohol-water) | Embodiments 3 groups medium dose (grinding powder and alcohol-water) | Embodiments 3 groups high dose (grinding powder and alcohol-water) | Embodiments 1 groups (grinding powder) | Embodiments 2 groups (alcohol-wate) |
|---|---|---|---|---|---|
| Before treatment | 209.5 ± 5.68 | 208.3 ± 8.65 | 207.6 ± 7.81 | 209.9 ± 6.80 | 208.9 ± 8.36 |
| Treatment for 1 week | 14.0/19.3 = 0.73 | 17.9/29.2 = 0.61 | 27.1/39.4 = 0.69 | 21.4/24.3 = 0.88 | 6.2/35.1 = 0.18 |
| Treatment for 2 weeks | 13.2/19.8 = 0.67 | 16.8/26.0 = 0.65 | 28.3/38.1 = 0.74 | 20.2/23.6 = 0.86 | 5.4/36.7 = 0.15 |

The trough-peak ratio of hypotension is the trough value of blood pressure reduction 24 hours after treatment divided by the peak value of blood pressure reduction 2 hours after treatment.

Experiment 4

Experimental Study on the Antihypertensive Effect of the Sample of Example 1 on Spontaneously Hypertensive Rats (SHR) and Normal Rats

[Experimental Materials]

Rats: Spontaneously Hypertensive Rats (SHR), Wistar rats were used as normal controls.

Chinese medicine in the test is as follows.

Test sample of Example 1: Take 500 g of *Dendrobium* in accordance with the 2015 edition of the Chinese Pharmacopoeia, the powder of *Dendrobium officinale* is ground and added with appropriate excipients according to the routine pharmacy to make Chinese medicine granules (suspended granules) and dried to obtain the sample of example 11, and it is dissolved in hot water before use.

Western antihypertensive control drugs: amlodipine besylate tablets (Norvasc), 5 mg/tablets, batch number: R78401, produced by Pfizer Pharmaceutical Production.

Rat Blood Pressure Measurement: BP-98A Non-invasive Tail Artery Blood Pressure Meter, Japan Soft Rotation Co., Ltd.

[Experimental Method]

Group therapy is described in the following description. Blood pressure and body weight are measured and grouped after one week of adaptive feeding in all rats. The SHR rats are divided to the small-dose group in embodiment 1, the middle-dose group in embodiment 1, the large-dose group in embodiment 1, and add a group in embodiment 1 for normal wister rats, each Chinese medicine group is given with 0.4, 0.8, 1.6 and 0.8 g/kg body weight of crude drug respectively, the amlodipine besylate tablets 0.5 mg/kg body weight are given intragastrically in amlodipine group, the hypertensive model control group is given with the same amount of saline, while the normal control group is given with the same amount of saline. Eight rats in each group are treated for 2 weeks.

The following description describes the blood pressure measurement. The rats are preheated at 38° C. for 5-10 minutes to avoid blood flow in the tail of the rat. The blood pressure of the rats is measured three times in a waking and quiet state, and the average value of three times is used as the blood pressure of the rats. Blood pressure is measured twice a week, once 2 hours after administration and once 24 hours after administration, to observe the immediate antihypertensive effect and after 24 hours antihypertensive effect (and the peak-to-valley ratio).

The following description discusses the trough-peak ratio calculation of depressurization amplitude. The difference of blood pressure before treatment minus 24 hours after administration is the trough of the range of blood pressure reduction, which is the lowest point before the next administration; the difference of blood pressure before treatment and 2 hours after administration is the peak value of blood pressure reduction, that is, the maximum point of blood pressure reduction after administration. Valley value of depressurization amplitude divided by peak value of depressurization amplitude is equal to valley-peak ratio of depressurization amplitude. The closer the trough-peak ratio is to 1, the more stable the antihypertensive effect is, and the more in line with the requirements of long-term antihypertensive drugs; the closer the trough-peak ratio is to 0, the shorter the antihypertensive effect is.

[Experimental Results]

Blood pressure data (x±S) are shown in Table 1, Table 2, Table 3, Table 4 and Table 5 of Experiment 4.

1. Blood pressure 2 hours after administration.

Two hours after treatment at 2 weeks, the blood pressure in the high dose group is 174.7±3.35/142.6±4.82 mmHg in the first embodiment, 180.6±4.38/147.1±3.53 mmHg in the middle dose group in the first embodiment and 187.6±4.28/150.2±4.46 mmHg in the low dose group in the first embodiment, which are significantly lower than that in the model group (212.7±5.47/162.3±4.87 mmHg, $P<0.01$ or $P<0.05$). The blood pressure of the high dose group is lower than that of the low dose group ($P<0.01/P<0.05$).

The hypotensive effect of large dose group and medium dose group 2 hours after administration is similar to that of amlodipine group ($P>0.05$).

Sample 1 of embodiment has no effect on blood pressure of normal rats 2 hours after administration.

2. Blood pressure 24 hours after administration.

24 hours after treatment at 2 weeks, blood pressure in the high dose group is 180.5±4.68/145.5±4.76 mmHg in the first embodiment, 189.3±5.32/151.8±4.59 mmHg in the dose group in the first embodiment and 190.2±5.38/153.7±3.99 mmHg in the low dose group in the first embodiment, which are significantly lower than that in the model group (214.5±5.36/164.3±4.83 mmHg, $P<0.01$ or $P<0.05$). In embodiment 1, systolic blood pressure in high dose group is lower than that in low dose group ($P<0.05$).

The 24-hour systolic blood pressure in the high-dose group and the middle-dose group is significantly lower than that in the amlodipine group ($P<0.01$ or $P<0.05$). The 24-hour diastolic blood pressure in the high-dose group and the middle-dose group is lower than that in the amlodipine group, but there was no statistical significance.

Sample 1 of embodiment has no effect on blood pressure of normal rats 24 hours after administration.

3. At 2 weeks of 24 hours of antihypertensive dose/2 hours of antihypertensive effect is trough-peak ratio of depressurization.

In the large-dose group of embodiment 1, the 24-hour hypotensive amplitude of 31.0 mmHg divided by the 2-hour hypotensive amplitude of 36.8 mmHg in the high dose group is equal to the trough-peak ratio of the hypotensive amplitude which is 0.84.

In the medium-dose group of embodiment 1, the 24-hour hypotension amplitude of 22.5 mmHg divided by the 2-hour hypotension amplitude of 31.2 mmHg in the dose group is equal to the trough-peak ratio of the hypotension amplitude which is 0.72.

In the small-dose group of embodiment 1, the 24-hour hypotensive amplitude of 20.0 mmHg divided by the 2-hour hypotensive amplitude of 22.6 mmHg in the low dose group is equal to the trough-peak ratio of the hypotensive amplitude which is 0.88.

In the amlodipine group, the 24-hour hypotension range of 6.8 mmHg divided by the 2-hour hypotension range of 33.0 mmHg is equal to the trough-peak ratio which is 0.21.

At 2 weeks of treatment, the 24-hour hypotension of sample 1 is greater than that of amlodipine group. The trough to peak ratios of blood pressure reduction range in the large, medium and small dose groups of sample 1 are 0.84 (84%), 0.72 (72%) and 0.88 (88%) respectively, which are higher than that in the amlodipine group of Western medicine 0.21 (21%). The hypotensive effect of sample 1 is more stable.

The dose of rats used in this experiment corresponds to the equivalent adult dose.

The corresponding adult dose of the large-dose group of embodiment 1 is about 16 g everyday of raw drug of *Dendrobium officinale*.

The corresponding adult dose of the medium-dose group of embodiment 1 is about 8 g everyday of raw drug of *Dendrobium officinale*.

The corresponding adult dose of the small-dose group of embodiment 1 is about 4 g everyday of raw drug of *Dendrobium officinale*.

The corresponding adult dose in amlodipine group is about 5 mg everyday for amlodipine besylate tablets.

[Conclusion]

In embodiment 1, the high dose, medium dose and low dose groups of samples have significant antihypertensive effects 2 hours after administration and 24 hours after administration.

The hypotensive effect of sample large dose and medium dose groups 2 hours after administration approximates or achieves the hypotensive effect of amlodipine (equivalent to 5 mg/day for adults). 24 hours after administration, the antihypertensive effect of amlodipine has exceeded that of Western medicine; the ratio of trough to peak of antihypertensive is greater than that of amlodipine, and the stability of antihypertensive is higher than that of amlodipine.

The sample of embodiment 1 has no significant effect on blood pressure in normal rats.

Experiment 4: Table 1. Effects of Samples from Executions 1 on Systolic Blood Pressure in SHR and normal rats after 2-hour Administration ($x \pm S$; unit: mmHg; n = 8)

| Treatment time | Embodiments 1 groups small dose | Embodiments 1 groups medium dose | Embodiment s 1 groups large dose | Embodiments 1 groups normal rats | Amlodipine | Model group | Normal group |
|---|---|---|---|---|---|---|---|
| Before treatment | 210.2 ± 6.76 | 211.8 ± 7.43 | 211.5 ± 8.12 | 142.7 ± 5.62▲ | 211.7 ± 7.57 | 210.7 ± 8.90 | 143.2 ± 4.31▲ |
| Treatment for 1 week | 188.5 ± 5.21▲★ | 182.3 ± 6.09▲ | 175.1 ± 4.56▲ | 141.5 ± 6.88▲●★ | 176.7 ± 7.42▲ | 209.2 ± 6.55●★ | 142.6 ± 5.26▲●★ |
| Treatment for 2 weeks | 187.6 ± 4.28▲★ | 180.6 ± 4.38▲☆ | 174.7 ± 3.35▲○ | 142.8 ± 5.87▲●★ | 178.7 ± 5.64▲ | 212.7 ± 5.47●★ | 144.8 ± 6.76▲●★ |

Note:
Compared with the model group, $^\triangle P < 0.05$ $^\blacktriangle P < 0.01$;
medium-dose group of example 1 compared with each group $^\circ P < 0.05$ $^\bullet P < 0.01$;
large-dose group of example 1 compared with each group $^\star p < 0.05$ $^\bigstar p < 0.01$ Experiment 4: Table 2. Effects of Samples from Executions 1 on Systolic Blood Pressure in SHR and normal rats after 24-hour Administration ($x \pm S$; unit: mmHg; n = 8)

| Treatment time | Embodiments 1 groups small dose | Embodiments 1 groups medium dose | Embodiments 1 groups large dose | Embodiments 1 groups normal rats | Amlodipine | Model group | Normal group |
|---|---|---|---|---|---|---|---|
| Before treatment | 210.2 ± 6.76 | 211.8 ± 7.43 | 211.5 ± 8.12 | 142.7 ± 5.62▲ | 211.7 ± 7.57 | 210.7 ± 8.90 | 143.2 ± 4.31▲ |
| Treatment for 1 week | 191.1 ± 6.41▲○☆ | 189.5 ± 6.36▲ | 181.3 ± 4.55▲ | 141.8 ± 9.56▲●★ | 202.6 ± 9.87○★ | 213.8 ± 6.55●★ | 141.7 ± 5.76▲●★ |
| Treatment for 2 weeks | 190.2 ± 5.38▲○☆ | 189.3 ± 5.32▲☆ | 180.5 ± 4.68▲○ | 143.5 ± 7.86▲●★ | 204.9 ± 9.78○★ | 214.5 ± 5.36●★ | 145.9 ± 6.78▲●★ |

Note:
Compared with the model group, $^\triangle P < 0.05$ $^\blacktriangle P < 0.01$;
medium-dose group of example 1 compared with each group $^\circ P < 0.05$ $^\bullet P < 0.01$;
large-dose group of example 1 compared with each group $^\star p < 0.05$ $^\bigstar p < 0.01$ Experiment 4: Table 3. Effects of Samples from Executions 1 on Diastolic Blood Pressure in SHR and normal rats after 2-hour Administration ($x \pm S$; unit: mmHg; n = 8)

| Treatment time | Embodiments 1 groups small dose | Embodiments 1 groups medium dose | Embodiments 1 groups large dose | Embodiments 1 groups normal rats | Amlodipine | Model group | Normal group |
|---|---|---|---|---|---|---|---|
| Before treatment | 157.4 ± 6.33 | 158.3 ± 4.82 | 159.3 ± 5.82 | 103.5 ± 5.87 | 158.2 ± 7.69 | 158.5 ± 6.35 | 102.8 ± 7.84▲ |
| Treatment for 1 week | 152.5 ± 5.68△★ | 149.6 ± 6.45△ | 143.7 ± 4.51▲ | 105.7 ± 5.76▲●★ | 145.9 ± 6.74▲ | 161.2 ± 5.35○★ | 103.7 ± 6.54▲●★ |

Experiment 4: Table 3. Effects of Samples from Executions 1 on Diastolic Blood Pressure in SHR and normal rats after 2-hour Administration (x ± S; unit: mmHg; n = 8)

| Treatment time | Embodiments 1 groups small dose | Embodiments 1 groups medium dose | Embodiments 1 groups large dose | Embodiments 1 groups normal rats | Amlodipine | Model group | Normal group |
|---|---|---|---|---|---|---|---|
| Treatment for 2 weeks | 150.2 ± 4.46<sup>Δ☆</sup> | 147.1 ± 3.53▲ | 142.6 ± 4.82▲ | 106.7 ± 4.89▲●★ | 144.8 ± 5.76▲ | 162.3 ± 4.87●★ | 104.6 ± 6.11▲●★ |

Note:
Compared with the model group, $^{\Delta}P < 0.05$ $^{▲}P < 0.01$;
medium-dose group of example 1 compared with each group $^{○}P < 0.05$ $^{●}P < 0.01$;
large-dose group of example 1 compared with each group $^{☆}p < 0.05$ $^{★}p < 0.01$ Experiment 4: Table 4. Effects of Samples from Executions 1 on Diastolic Blood Pressure in SHR and normal rats after 24-hour Administration (x ± S; unit: mmHg; n = 8)

| Treatment time | Embodiments 1 groups small dose | Embodiments 1 groups medium dose | Embodiments 1 groups large dose | Embodiments 1 groups normal rats | Amlodipine | Model group | Normal group |
|---|---|---|---|---|---|---|---|
| Before treatment | 157.4 ± 6.33 | 158.3 ± 4.82 | 159.3 ± 5.82 | 103.5 ± 5.87 | 158.2 ± 7.69 | 157.5 ± 6.35 | 102.8 ± 7.84▲ |
| Treatment for 1 week | 153.6 ± 7.68 | 150.3 ± 4.18▲ | 147.3 ± 4.89▲ | 104.7 ± 5.64▲●★ | 156.5 ± 5.42 | 162.4 ± 4.77●★ | 104.7 ± 6.67▲●★ |
| Treatment for 2 weeks | 153.7 ± 3.99<sup>Δ</sup> | 151.8 ± 4.59▲ | 145.5 ± 4.76▲ | 105.1 ± 4.87▲●★ | 157.3 ± 6.73 | 164.3 ± 4.83●★ | 102.8 ± 5.24▲●★ |

Note:
Compared with the model group, $^{\Delta}P < 0.05$ $^{▲}P < 0.01$;
medium-dose group of example 1 compared with each group $^{○}P < 0.05$ $^{●}P < 0.01$;
large-dose group of example 1 compared with each group $^{☆}p < 0.05$ $^{★}p < 0.01$ Experiment 4: Table 5. Effects of samples from executions 1 on valley-peak ratio of Systolic Blood Pressure Reduction in SHR and normal rats 24 hours after Administration divided by 2 hours after Administration (x ± S; unit: mmHg; n = 8)

| Treatment time | Embodiments 1 groups small dose | Embodiments 1 groups medium dose | Embodiments 1 groups large dose | Amlodipine |
|---|---|---|---|---|
| Before treatment | 210.2 ± 6.76 | 211.8 ± 7.43 | 211.5 ± 8.12 | 211.7 ± 17.57 |
| Treatment for 1 week | 19.1/21.7 = 0.88 | 22.3/29.5 = 0.76 | 30.2/36.4 = 0.83 | 9.1/35.0 = 0.26 |
| Treatment for 2 weeks | 20.0/22.6 = 0.88 | 22.5/31.2 = 0.72 | 31.0/36.8 = 0.84 | 6.8/33.0 = 0.21 |

The trough-peak ratio of hypotension is the trough value of blood pressure reduction 24 hours after treatment divided by the peak value of blood pressure reduction 2 hours after treatment.

Experiment 5

Experimental Study on the Antihypertensive Effect of the Sample of Example 2 on Spontaneously Hypertensive Rats (SHR) and Normal Rats

[Experimental Materials]

Rats: Spontaneously Hypertensive Rats (SHR), Wistar rats are used as normal controls.

Chinese medicine in the test is as follows.

Test sample of Example 2 is discussed in the following description. 500 g of *Dendrobium officinale* in accordance with Chinese Pharmacopoeia 2015 edition is extracted for 24 hours with 75% ethanol of 5 times the total amount of crude drugs at 60° C. for 2 times, and then the residue is extracted by water after ethanol extraction. Water extraction is carried out by twice gradient heating method. Accordingly, in the first time of water extraction, add water with 30 times of the total amount of crude drug, and the extraction time is 2 hours at 100° C. Then in the second time of water extraction, add water with 20 times of the total amount of crude drug added, and the second water extraction is carried out at 121° C. for 2 hours. And then carry out the consolidation and concentration of water extracts. After the alcohol extraction and the water extraction are separately concentrated, the extracts are combined, and appropriate excipients are added according to the pharmacy routine to prepare Chinese medicine granules and then is dried to obtain the sample of example 2, and it is dissolved in hot water before use.

Western antihypertensive control drugs: amlodipine besylate tablets (Norvasc), 5 mg/tablets, batch number: R78401, produced by Pfizer Pharmaceutical Production.

Rat Blood Pressure Measurement: BP-98A Non-invasive Tail Artery Blood Pressure Meter, Japan Soft Rotation Co., Ltd

[Experimental Method]

Group therapy is described in the following description. Blood pressure and body weight are measured and grouped after one week of adaptive feeding in all rats. The SHR rats are divided to the small-dose group in embodiment 2, the middle-dose group in embodiment 2, the large-dose group in embodiment 2, and add a group in embodiment 2 for normal wister rats, each Chinese medicine group is given with 0.4, 0.8, 1.6 and 0.8 g/kg body weight of crude drug respectively, the amlodipine besylate tablets 0.5 mg/kg body weight are given intragastrically in amlodipine group, the hypertensive model control group is given with the same amount of saline, while the normal control group is given with the same amount of saline. Eight rats in each group are treated for 2 weeks.

The following description discussed with the blood pressure measurement. The rats are preheated at 38° C. for 5-10 minutes to avoid blood flow in the tail of the rat. The blood pressure of the rats is measured three times in a waking and quiet state, and the average value of three times was used as the blood pressure of the rats. Blood pressure is measured twice a week, once 2 hours after administration and once 24 hours after administration, to observe the immediate antihypertensive effect and after 24 hours antihypertensive effect (and the peak-to-valley ratio).

The following description discusses with the trough-peak ratio calculation of depressurization amplitude. The difference of blood pressure before treatment minus 24 hours after administration is the trough of the range of blood pressure reduction, which is the lowest point before the next administration; the difference of blood pressure before treatment and 2 hours after administration is the peak value of blood pressure reduction, that is, the maximum point of blood pressure reduction after administration. Valley value of depressurization amplitude divided by peak value of depressurization amplitude is equal to valley-peak ratio of depressurization amplitude. The closer the trough-peak ratio is to 1, the more stable the antihypertensive effect is, and the more in line with the requirements of long-term antihypertensive drugs; the closer the trough-peak ratio is to 0, the shorter the antihypertensive effect is.

[Experimental Results]

Blood pressure data (x±S) are shown in Table 1, Table 2, Table 3, Table 4 and Table 5 of Experiment 5.

Experiment 5: Table 1. Effects of Samples from Executions 2 on Systolic Blood Pressure in SHR and normal rats after 2-hour Administration (x ± S; unit: mmHg; n = 8)

| Treatment time | Embodiments 2 groups small dose | Embodiments 2 groups medium dose | Embodiments 2 groups large dose | Embodiments 2 groups normal rats | Amlodipine | Model group | Normal group |
|---|---|---|---|---|---|---|---|
| Before treatment | 213.2 ± 7.46 | 211.6 ± 6.58 | 213.8 ± 7.46 | 141.8 ± 6.76▲ | 212.7 ± 6.87 | 211.5 ± 7.67 | 141.3 ± 5.51▲ |
| Treatment for 1 week | 182.8 ± 5.33▲★ | 176.6 ± 8.11▲ | 171.1 ± 4.35▲ | 140.3 ± 7.89▲●★ | 178.2 ± 5.36▲ | 210.6 ± 7.55●★ | 143.5 ± 6.48▲●★ |
| Treatment for 2 weeks | 183.5 ± 4.53▲★ | 175.4± 5.36▲ | 170.8 ± 4.10▲ | 141.7 ± 6.87▲●★ | 180.5 ± 4.79▲☆ | 213.8 ± 6.58●★ | 142.5 ± 5.89▲●★ |

Note:
Compared with the model group, ᐃP < 0.05 ▲P < 0.01;
medium-dose group of example 2 compared with each group ○P < 0.05 ●P < 0.01;
large-dose group of example 2 compared with each group ☆p < 0.05★p < 0.01

Experiment 5: Table 2. Effects of Samples from Executions 2 on Systolic Blood Pressure in SHR and normal rats after 24-hour Administration (x ± S; unit: mmHg; n = 8)

| Treatment time | Embodiments 2 groups small dose | Embodiments 2 groups medium dose | Embodiments 2 groups large dose | Embodiments 2 groups normal rats | Amlodipine | Model group | Normal group |
|---|---|---|---|---|---|---|---|
| Before treatment | 213.2 ± 7.46 | 211.6 ± 6.58 | 213.8 ± 7.46 | 141.8 ± 6.76▲ | 212.7 ± 6.87 | 211.5 ± 7.67 | 141.3 ± 5.51▲ |
| Treatment for 1 week | 209.6 ± 6.75 | 206.4 ± 8.57 | 204.2 ± 5.67 | 142.5 ± 8.79▲●★ | 203.5 ± 7.56 | 212.5 ± 7.45●★ | 142.6 ± 6.51▲●★ |
| Treatment for 2 weeks | 208.8 ± 6.48 | 206.7 ± 6.59 | 203.8 ± 4.68ᐃ | 141.7 ± 7.46▲●★ | 205.6 ± 8.54 | 214.8 ± 6.28●★ | 143.7 ± 5.66▲●★ |

Note:
Compared with the model group, ᐃP < 0.05▲P < 0.01;
medium-dose group of example 2 compared with each group ○P < 0.05 ●P < 0.01;
large-dose group of example 2 compared with each group ☆p < 0.05★p < 0.01

Experiment 5: Table 3. Effects of Samples from Executions 2 on Diastolic Blood Pressure in SHR and normal rats after 2-hour Administration (x ± S; unit: mmHg; n = 8)

| Treatment time | Embodiments 2 groups small dose | Embodiments 2 groups medium dose | Embodiments 2 groups large dose | Embodiments 2 groups normal rats | Amlodipine | Model group | Normal group |
|---|---|---|---|---|---|---|---|
| Before treatment | 159.2 ± 5.72 | 161.5 ± 5.78 | 160.7 ± 6.72 | 104.7 ± 6.74 | 159.6 ± 6.75 | 159.8 ± 7.64 | 103.7 ± 6.87▲ |
| Treatment for 1 week | 151.1 ± 4.47△☆ | 145.3 ± 6.87▲ | 141.3 ± 5.76▲ | 104.1 ± 6.72▲●★ | 146.8 ± 5.74▲ | 162.7 ± 6.46●★ | 104.8 ± 7.84▲●★ |
| Treatment for 2 weeks | 150.3 ± 4.27△☆ | 146.2 ± 3.35▲ | 140.5 ± 4.76▲ | 105.1 ± 5.87▲●★ | 148.5 ± 6.72▲ | 163.4 ± 5.11●★ | 105.4 ± 7.25▲●★ |

Note:
Compared with the model group, △P < 0.05 ▲P < 0.01;
medium-dose group of example 2 compared with each group ○P < 0.05 ●P < 0.01;
large-dose group of example 2 compared with each group ☆p < 0.05 ★p < 0.01

Experiment 5: Table 4. Effects of Samples from Executions 2 on Diastolic Blood Pressure in SHR and normal rats after 24-hour Administration (x ± S; unit: mmHg; n = 8)

| Treatment time | Embodiments 2 groups small dose | Embodiments 2 groups medium dose | Embodiments 2 groups large dose | Embodiments 2 groups normal rats | Amlodipine | Model group | Normal group |
|---|---|---|---|---|---|---|---|
| Before treatment | 159.2 ± 5.72 | 161.5 ± 5.78 | 160.7 ± 6.72 | 104.7 ± 6.74 | 159.6 ± 6.75 | 159.8 ± 7.64 | 103.7 ± 6.87▲ |
| Treatment for 1 week | 159.1 ± 6.76 | 159.6 ± 5.67 | 157.9 ± 5.79 | 105.8 ± 6.55▲●★ | 157.1 ± 6.42 | 164.3 ± 5.21●★ | 105.7 ± 7.84▲●★ |
| Treatment for 2 weeks | 158.7 ± 5.67 | 158.4 ± 5.67 | 156.8 ± 5.87 | 104.7 ± 5.97▲●★ | 157.6 ± 7.64 | 163.5 ± 5.12●★ | 104.7 ± 6.35▲●★ |

Note:
Compared with the model group, △P < 0.05 ▲P < 0.01;
medium-dose group of example 2 compared with each group ○P < 0.05 ●P < 0.01;
large-dose group of example 2 compared with each group ☆p < 0.05 ★p < 0.01

Experiment 5: Table 5. Effects of samples from executions 2 on valley-peak ratio of Systolic Blood Pressure Reduction in SHR and normal rats 24 hours after Administration divided by 2 hours after Administration (x ± S; unit: mmHg; n = 8)

| Treatment time | Embodiments 2 groups small dose | Embodiments 2 groups medium dose | Embodiments 2 groups large dose | Amlodipine |
|---|---|---|---|---|
| Before treatment | 213.2 ± 7.46 | 211.6 ± 6.58 | 213.8 ± 7.46 | 212.7 ± 6.87 |
| Treatment for 1 week | 3.6/30.4 = 0.12 | 5.2/35.0 = 0.15 | 9.6/42.4 = 0.23 | 9.2/34.5 = 0.27 |
| Treatment for 2 weeks | 4.4/29.7 = 0.15 | 4.9/36.2 = 0.14 | 10.0/43.0 = 0.23 | 7.1/32.2 = 0.22 |

The trough-peak ratio of hypotension is the trough value of blood pressure reduction 24 hours after treatment divided by the peak value of blood pressure reduction 2 hours after treatment.

1. Blood pressure 2 hours after administration.

Two hours after treatment at 2 weeks, the blood pressure in the high dose group is 170.8±4.10/140.5±4.76 mmHg in the second embodiment, 175.4±5.36/146.2±3.35 mmHg in the middle dose group and 183.5±4.53/150.3±4.27 mmHg in the low dose group in the second embodiment, which are significantly lower than those in the model group (213.8±6.58/163.4±5.11 mmHg, P<0.01 or P<0.05). The blood pressure of the high dose group is lower than that of the low dose group (P<0.01/P<0.05).

The systolic blood pressure in the high dose group of embodiment 2 is lower than that in the amlodipine group 2 hours after administration (P<0.05), and the diastolic blood pressure is lower than that in the amlodipine group 2 hours after administration, but it has no statistical significance.

Sample 2 of embodiment 2 has no effect on blood pressure of normal rats 2 hours after administration.

2. Blood pressure 24 hours after administration.

The blood pressure of 24 hours after administration at 2 weeks is 203.8±4.68/156.8±5.87 mmHg in the high dose group of embodiment 2, which is lower than that of model group 214.8±6.28/163.5±5.12 mmHg (systolic pressure P<0.05). In embodiment 2, the blood pressure of dose group, low dose group and amlodipine group is slightly lower than that of model group, but there is no statistical significance.

Sample 2 of embodiment 2 has no effect on blood pressure of normal rats 24 hours after administration.

3. At 2 weeks of 24 hours of antihypertensive dose/2 hours of antihypertensive effect is trough-peak ratio of depressurization.

In the large-dose group of embodiment 2, the 24-hour hypotensive amplitude of 10.0 mmHg divided by the 2-hour hypotensive amplitude of 43.0 mmHg in high dose group is equal to the trough-peak ratio of the hypotensive amplitude which is 0.23;

In the medium-dose group of embodiment 2, the 24-hour hypotensive amplitude of 4.9 mmHg divided by the 2-hour hypotensive amplitude of 36.2 mmHg in the dose group is equal to the trough-peak ratio of the hypotensive amplitude which is 0.14.

In the small-dose group of embodiment 2, the 24-hour hypotensive amplitude of 4.4 mmHg divided by the 2-hour hypotensive amplitude of 29.7 mmHg in the low dose group is equal to the trough-peak ratio of the hypotensive amplitude which is 0.15.

In the amlodipine group, the 24-hour hypotension amplitude of 7.1 mmHg divided by the 2-hour hypotension amplitude of 32.2 mmHg is equal to the trough-peak ratio which is 0.22.

At 2 weeks of treatment, the 24-hour hypotension amplitude of sample 2 is relatively small, while the 2-hour hypotension amplitude of sample 2 is relatively large, and the short-term hypotension effect is better.

The dose of rats used in this experiment corresponds to the equivalent adult dose.

The corresponding adult dose of the large-dose group of embodiment 2 is about 16 g everyday of raw drug of *Dendrobium officinale*.

The corresponding adult dose of the medium-dose group of embodiment 2 is about 8 g everyday of raw drug of *Dendrobium officinale*.

The corresponding adult dose of the small-dose group of embodiment 2 is about 4 g everyday of raw drug of *Dendrobium officinale*.

The corresponding adult dose in amlodipine group is about 5 mg everyday for amlodipine besylate tablets.

[Conclusion]

In the embodiment 2, the blood pressure of the sample in large dose, medium dose and small dose groups is significantly lowered 2 hours after administration. The 24-hour antihypertensive effect was relatively small.

The antihypertensive effect of sample 2 large dose group 2 hours after administration is better than that of amlodipine (equivalent to 5 mg/day for adults). The trough-peak ratio of hypotension is small, and the range of hypotension is relatively large after 2 hours of administration, and the short-term hypotensive effect is better.

The sample of embodiment 2 has no significant effect on blood pressure of normal rats.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and are subject to change without departure from such principles. Therefore, this invention includes all modifications encompassed within the spirit and scope of the following claims.

What is claimed is:

1. A method of treating hypertension, comprising:
administering *Dendrobium officinale* as a medicament with a daily dosage for adult orally equivalent to a raw drug dosage of 4 g to 16 g wherein the medicament is prepared by grinding *Dendrobium officinale* according to requirements of 2015 edition of Chinese Pharmacopoeia to a predetermined amount of powdered crude drug; alcohol extracting the powdered crude drug by adding 75% ethanol with an amount 5 times of the amount of the powdered crude drug, extracting twice at 60° C. for 24 hours, and recovering the ethanol to form a residue; water extracting the residue by adding 30 times of a total amount of the powdered crude drug of water with an extraction temperature controlled to be 100° C. for 2 hours to form a first time water extraction solution; water extracting the residue by adding 20 times of the total amount of the powdered crude drug of water with an extraction temperature controlled to be 121° C. for 2 hours to form a second time water extraction solution; concentrating and combining the first time water extraction solution and the second time water extraction solution to form a combined extract, and adding a predetermined amount of one or more excipients to the combined extract to obtain the medicament for treating hypertension.

2. The method, as recited in claim 1, wherein the combined extract is mixed with the excipients to form the medicament in form of tablets, granules, suspended granules, pills, power or capsules.

3. The method, as recited in claim 1, wherein, before adding the one or more excipients, another predetermined amount of the powdered crude drug is added to the combined extract.

4. The method, as recited in claim 2, wherein, before adding the one or more excipients, another predetermined amount of the powdered crude drug is added to the combined extract.

* * * * *